US010682220B2

(12) United States Patent
Folan et al.

(10) Patent No.: US 10,682,220 B2
(45) Date of Patent: Jun. 16, 2020

(54) ESOPHAGEAL STENT INCLUDING AN INNER LINER

(71) Applicants: BOSTON SCIENTIFIC SCIMED, INC., Maple Grove, MN (US); UNIVERSITE LIBRE DE BRUXELLES, Brussels (BE)

(72) Inventors: Martyn G. Folan, Galway (IE); Thomas M. Keating, Galway (IE); Jacques Deviere, Brussels (BE); Nicolas Cauche, Brussels (BE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 92 days.

(21) Appl. No.: 15/909,574

(22) Filed: Mar. 1, 2018

(65) Prior Publication Data
US 2018/0250118 A1    Sep. 6, 2018

Related U.S. Application Data

(60) Provisional application No. 62/466,025, filed on Mar. 2, 2017.

(51) Int. Cl.
*A61F 2/04*    (2013.01)
*A61F 2/07*    (2013.01)
*A61F 2/90*    (2013.01)

(52) U.S. Cl.
CPC .................. *A61F 2/04* (2013.01); *A61F 2/07* (2013.01); *A61F 2/90* (2013.01);
(Continued)

(58) Field of Classification Search
CPC ..................... A61F 2002/075; A61F 2002/077
See application file for complete search history.

(56) References Cited

U.S. PATENT DOCUMENTS 5,667,523 A * 9/1997 Bynon ...................... A61F 2/07
606/194
6,264,689 B1    7/2001 Colgan et al.
(Continued)

FOREIGN PATENT DOCUMENTS

WO    2004049982 A2    6/2004
WO    2015195893 A1    12/2015

OTHER PUBLICATIONS

Hirdes et al., "Stent-in-Stent Technique for Removal of Embedded Esophageal Self-Expanding Metal Stents," Am J Gastroenterol 2011; 106:286-293.
(Continued)

*Primary Examiner* — Leslie Lopez
(74) *Attorney, Agent, or Firm* — Seager, Tufte & Wickhem, LLP

(57) ABSTRACT

An example medical device is disclosed as an expandable stent. The stent includes a tubular scaffold having an inner surface, an outer surface, and a lumen extending therein. The expandable stent also includes a liner disposed within the lumen of the tubular scaffold. Further, the liner is radially spaced from a medial region of the tubular scaffold to define a tissue ingrowth region along an uncovered portion of the medial region. Additionally, the liner extending along the tissue ingrowth region is configured to limit the amount of tissue ingrowth along the medial region of the scaffold.

19 Claims, 26 Drawing Sheets

(52) U.S. Cl.
CPC ... *A61F 2002/044* (2013.01); *A61F 2002/075* (2013.01); *A61F 2220/0008* (2013.01); *A61F 2220/0016* (2013.01); *A61F 2230/001* (2013.01); *A61F 2250/0039* (2013.01)

(56) References Cited

U.S. PATENT DOCUMENTS

| | | | |
|---|---|---|---|
| 6,283,992 | B1 | 9/2001 | Hankh et al. |
| 6,585,758 | B1 | 7/2003 | Chouinard et al. |
| 7,311,031 | B2 | 12/2007 | McCullagh et al. |
| 2003/0149472 | A1 | 8/2003 | Pinchuk et al. |
| 2005/0085923 | A1* | 4/2005 | Levine ............... A61B 17/0401 623/23.65 |
| 2009/0210048 | A1 | 8/2009 | Amplatz et al. |
| 2011/0319980 | A1 | 12/2011 | Ryan |
| 2014/0121759 | A1 | 5/2014 | Cully |
| 2014/0222039 | A1 | 8/2014 | Khrosrovaninejad |
| 2014/0277443 | A1 | 9/2014 | Fleury et al. |
| 2014/0350694 | A1 | 11/2014 | Behan |
| 2015/0045908 | A1 | 2/2015 | McMahon |
| 2015/0282922 | A1 | 10/2015 | Hingston et al. |
| 2016/0095724 | A1 | 4/2016 | Harris et al. |
| 2016/0296317 | A1 | 10/2016 | Timmermans et al. |

OTHER PUBLICATIONS

International Search Report and Written Opinion dated Jun. 18, 2018 for International Application No. PCT/US2018/024456, 13 pages.
Davee et al., "Stent-in-stent Technique for Removal of Embedded Partially Covered Self-Expanding Metal Stents", Surg Endosc, vol. 30, 2332-2341, 2016.
Deviere et al., "Anchoring System for Disease Treatment," Boston Scientific Corporation, 1-22, 2016.
Deviere et al., "Effectiveness of Endoscopic Management Using Self-Expandable Metal Stents in a Large Cohort of Patients with Post-bariatric Leaks," Obes Surg., vol. 25, 1569-1576, 2015.
Eisendrath et al., "Endotherapy Including Temporary Stenting of Fistulas of the Upper Gastrointestinal TractAfter Laparoscopic Bariatric Surgery," Endoscopy, vol. 39, 625-630, 2007.
International Search report and Written Opinion dated May 29, 2018 for International Application No. PCT/US2018/020474 (11 pgs).

* cited by examiner

ESOPHAGEAL STENT INCLUDING AN INNER LINER

CROSS REFERENCE TO RELATED APPLICATIONS

The present application claims the benefit of and priority to U.S. Provisional Patent Application Ser. No. 62/466,025, filed Mar. 2, 2017, the disclosure of which is incorporated herein by reference.

TECHNICAL FIELD

The present disclosure pertains to medical devices, methods for manufacturing medical devices, and the use thereof. More particularly, the present disclosure pertains to stents including an inner member, such as an inner liner, and methods for manufacturing and using such stents.

BACKGROUND

Implantable medical devices (e.g., expandable stents) may be designed to provide a pathway for digested material, blood, or other fluid to flow therethrough following a medical procedure. Further, some implantable medical devices may incorporate features that aid in fistula treatment, bypass procedures and/or anastomosis treatment. These medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design a stent which includes sufficient radial strength to maintain its positon within a body lumen while also having the ability to function as a passageway for food or other digested material to flow therethrough. However, in some stents, the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices or openings thereof (e.g., the stent structure may promote a hyperplastic response). The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). However, covered stents may be more prone to migration than bare stents (as discussed above).

Further, in addition to designing stents capable of being both sufficiently anchored and easily removed from a body lumen, it may be desirable to design stents with features that aid digestible material in passing through a body lumen. For example, in some instances it may be desirable to design stents with an inner liner (e.g., lumen) which permits food or other digested materials to flow therethrough.

Therefore, in some instances it may be desirable to design a stent which includes both a covered portion, a non-covered (e.g., bare) portion and a tubular liner. Examples of the medical devices including covered portions, non-covered portions and inner liners are disclosed herein.

BRIEF SUMMARY

This disclosure provides design, material, manufacturing method, and use alternatives for medical devices. An example expandable medical device includes a tubular scaffold. The scaffold including an inner surface, an outer surface and a lumen extending therein. The expandable medical device also includes a liner disposed within the lumen of the tubular scaffold. Further, the liner is radially spaced from a medial region of the tubular scaffold to define a tissue ingrowth region along the medial region.

Additionally, the liner extending along the tissue ingrowth region is configured to limit the amount of tissue ingrowth along the medial region of the scaffold.

Alternatively or additionally to any of the embodiments above, the liner is configured to limit the amount of tissue ingrowth into the medial region of the tubular scaffold due to a hyperplastic response.

Alternatively or additionally to any of the embodiments above, the tissue ingrowth region is formed between the inner surface of the tubular scaffold and an outwardly-facing surface of the liner.

Alternatively or additionally to any of the embodiments above, the portion of the liner extending along the tissue ingrowth region is configured to deflect radially inward from the inner surface of the tubular scaffold.

Alternatively or additionally to any of the embodiments above, the medial portion of the tubular scaffold includes a first inner diameter, and the diameter of the liner along the tissue ingrowth region includes a second inner diameter, and wherein the second inner diameter is greater than 25% of the diameter of the first inner diameter.

Alternatively or additionally to any of the embodiments above, the liner is designed to maintain a passageway therethrough.

Alternatively or additionally to any of the embodiments above, the liner is fixedly attached to at least a portion of the inner surface of the tubular scaffold.

Alternatively or additionally to any of the embodiments above, the tissue ingrowth region extends circumferentially around the inner surface of the tubular scaffold.

Alternatively or additionally to any of the embodiments above, the liner is disposed along a portion of the outer surface of the tubular scaffold.

Alternatively or additionally to any of the embodiments above, the liner extends continuously along the inner surface of the tubular scaffold, along an end portion of the tubular scaffold and along a portion of the outer surface of the tubular scaffold.

Alternatively or additionally to any of the embodiments above, the liner is circumferentially attached to the tubular scaffold at a first location and a second location, and wherein the tissue ingrowth region is defined between the first location and the second location.

Alternatively or additionally to any of the embodiments above, the medial region is devoid of a liner such that tissue is permitted to grow through the interstices of the stent along the medial region.

Another esophageal stent includes an expandable tubular scaffold, the scaffold including an inner surface, an outer surface and a lumen extending therein. The stent also includes a liner disposed within the lumen of the tubular scaffold. The liner extends continuously within the lumen of the tubular scaffold. The liner is radially spaced from a medial region of the tubular scaffold to define a tissue ingrowth region along the medial region. The liner is configured to maintain a passageway through the liner for material to flow therethrough.

Alternatively or additionally to any of the embodiments above, wherein the liner is configured to limit the amount of tissue ingrowth into the medial region of the tubular scaffold due to a hyperplastic response.

Alternatively or additionally to any of the embodiments above, wherein the tissue ingrowth region is formed between the inner surface of the tubular scaffold and an outwardly-facing surface of the liner.

Alternatively or additionally to any of the embodiments above, wherein the portion of the liner extending along the tissue ingrowth region is configured to deflect radially inward from the inner surface of the tubular scaffold.

Alternatively or additionally to any of the embodiments above, wherein the medial portion of the tubular scaffold includes a first inner diameter, and wherein the diameter of the liner along the tissue ingrowth region includes a second inner diameter, and wherein the second inner diameter is greater than 25% of the diameter of the first inner diameter.

Alternatively or additionally to any of the embodiments above, wherein the liner is disposed along a portion of the outer surface of the tubular scaffold.

Another esophageal stent includes an expandable tubular scaffold having a lumen extending therein. The scaffold includes a first end portion, a second end portion and a medial portion positioned between the first and second end portions. The stent also includes a liner extending continuously within the lumen of the scaffold. The liner is circumferentially attached along the first end portion and the second end portion. A tissue ingrowth region is defined along the medial portion of the scaffold. The liner is radially spaced from the medial region of the tubular scaffold to define the tissue ingrowth region along the medial region. The liner is configured to maintain a passageway through the liner for material to flow therethrough.

Alternatively or additionally to any of the embodiments above, wherein the portion of the liner extending along the tissue ingrowth region is configured to deflect radially inward from an inner surface of the tubular scaffold.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
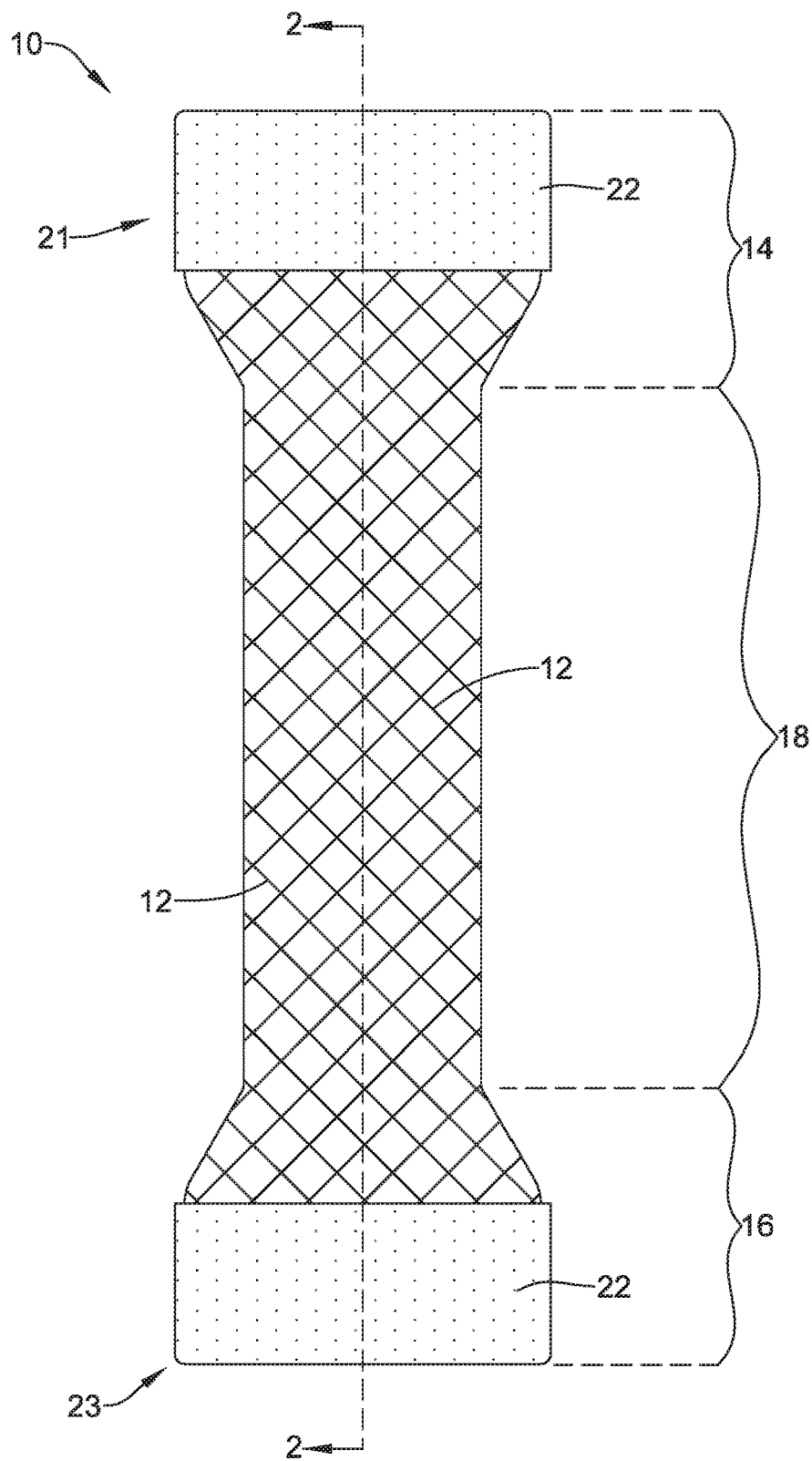
FIG. 1 is an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, in some instances it may be designed to provide a pathway for digested material, blood, or other fluid to flow therethrough following a medical procedure. Further, some implantable medical devices may incorporate features that aid in fistula treatment, bypass procedures and/or anastomosis treatment. These medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design a stent which includes sufficient radial strength to maintain its positon within a body lumen while also having the ability to function as a passageway for food or other digested material to flow therethrough. However, in some stents, the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth (e.g., a hyperplastic response) into the interstices or openings thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). However, covered stents may be more prone to migration than bare stents (as discussed above).

Further, in addition to designing stents capable of being both sufficiently anchored and easily removed from a body lumen, it may be desirable to design stents with features that aid digestible material in passing through a body lumen. For example, in some instances it may be desirable to design stents with an inner liner (e.g., lumen) which permits food or other digested materials to flow therethrough.

Therefore, in some instances it may be desirable to design a stent which includes both a covered portion, a non-covered (e.g., bare) portion and a tubular liner. Examples of the medical devices including covered portions, non-covered portions and inner liners are disclosed herein.

FIG. 1 shows an example stent 10. Stent 10 may have a first end 21, a second end 23 and a lumen extending therein. When positioned in a body lumen (e.g., esophagus) first or proximal end 21 may be defined as the end of stent 10 closest to a patient's mouth and second or distal end 23 may be defined as the end of stent 10 closest to a patient's stomach.

Additionally, stent 10 may include one or more stent strut members 12 forming a tubular scaffold. Stent strut members 12 may extend helically, longitudinally, circumferentially, or otherwise along stent 10. While FIG. 1 shows stent strut members 12 extending along the entire length of stent 10, in other examples, the stent strut members 12 may extend only along a portion of stent 10.

Additionally, FIG. 1 shows example stent 10 including a first flared end region 14 proximate the first end 21 and/or a second flared region 16 proximate the second end 23 of stent 10. In some instances, first flared region 14 and second flared region 16 may be defined as an increase in the outer diameter, the inner diameter or both the inner and outer diameter along one or both of the first end 21 and/or second end 23 of stent 10. Further, FIG. 1 illustrates stent 10 including a medial region 18 positioned between first flared region 14 and second flared region 16.

However, it is contemplated that while FIG. 1 shows stent 10 including both a first flared region 14 and a second flared region 16, stent 10 may only include one flared region. For example, it is contemplated that stent 10 may include only flared region 14 or flared region 16. It is further contemplated that all or a portion of first flared region 14 and/or second flared region 16 may flare outwardly (e.g., away from the central, longitudinal axis of stent 10). Alternatively, it is further contemplated that all or a portion of first flared region 14 and/or second flared region 16 may flare inwardly (e.g., toward the central, longitudinal axis of stent 10).

In some instances, stent 10 may be a self-expanding stent or stent 10 may be a balloon expandable stent. Self-expanding stent examples may include stents having one or more struts 12 combined to form a rigid and/or semi-rigid stent structure. For example, stent struts 12 may be wires or filaments which are braided, wrapped, intertwined, interwoven, weaved, knitted, looped (e.g., bobbinet-style) or the like to form the stent structure. For example, while the example stents disclosed herein may resemble a braided stent, this is not intended to limit the possible stent configurations. Rather, the stents depicted in the Figures may be stents that are knitted, braided, wrapped, intertwined, interwoven, weaved, looped (e.g., bobbinet-style) or the like to form the stent structure. Alternatively, stent 10 may be a monolithic structure formed from a cylindrical tubular member, such as a single, cylindrical tubular laser-cut Nitinol tubular member, in which the remaining portions of the tubular member form the stent struts 12. Openings or interstices through the wall of the stent 10 may be defined between adjacent stent struts 12.

Stent 10 in examples disclosed herein may be constructed from a variety of materials. For example, stent 10 (e.g., self-expanding or balloon expandable) may be constructed from a metal (e.g., Nitinol, Elgiloy, etc.). In other instances, stent 10 may be constructed from a polymeric material (e.g., PET). In yet other instances, stent 10 may be constructed from a combination of metallic and polymeric materials. Additionally, stent 10 may include a bioabsorbable and/or biodegradable material.

In some instances, example stent 10 may include one or more layers positioned on and/or adjacent to the inner and/or outer surface of the tubular scaffold of stent 10. For example, FIG. 1 shows example stent 10 including an outer layer 22 (depicted as a dotted pattern in FIG. 1) disposed along a portion of the outer surface of stent 10 (e.g., along the first flared portion 14 and/or the second flared portion 16 of stent 10). In some instances, outer layer 22 may be an elastomeric or non-elastomeric material. For example, outer layer 22 may be a polymeric material, such as silicone, polyurethane, or the like.

Additionally, example stent 10 may include one or more layers positioned on and/or adjacent to the inner surface of stent 10. While not shown in FIG. 1 (but shown in FIG. 2), stent 10 may include an inner layer 20 disposed within the lumen of stent 10. In some instances, inner layer 20 may be an elastomeric or non-elastomeric material. For example, inner layer 20 may be a polymeric material, such as silicone, polyurethane, UE, PVDF, Chronoflex® or similar biocompatible polymeric formulations.

It can be appreciated that as inner layer 20 and outer layer 22 extend outwardly and inwardly, respectively, they may touch and/or form an interface region within the spaces (e.g., openings, cells, interstices) in the wall of tubular scaffolding of stent 10. Further, the inner layer 20 and outer layer 22 may additionally extend between adjacent struts 12, thereby filling any space between adjacent strut members 12 of the tubular scaffold. Stent 10 may include areas in which one or more filaments 12 are surrounded, encased and/or covered by the outer layer 22 and/or inner layer 20. For example, some portions of stent 10 may include filaments 12 which are sandwiched between outer layer 22 and inner layer 20.

Figure 2:
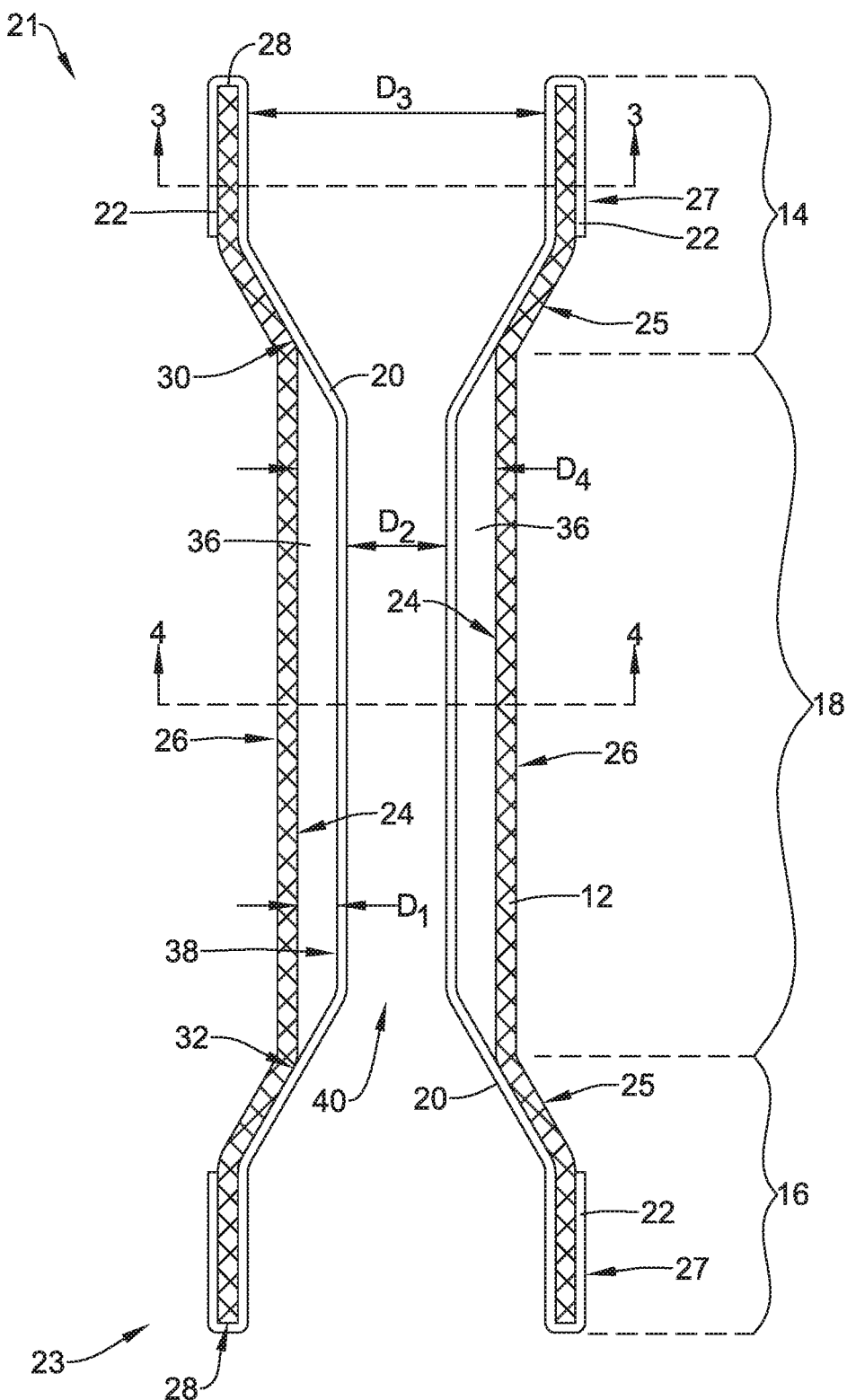
FIG. 2 is a cross-sectional view of the stent of FIG. 1 including a liner taken along line 2-2 of FIG. 1.

FIG. 2 shows a cross-section of example stent 10 along line 2-2 of FIG. 1. FIG. 2 illustrates that first flared region 14 and/or second flared region 16 may include tapered portion 25 and end portion 27. While FIG. 2 shows tapered portions tapering radially outward toward ends of stent 10, it is contemplated that one or more of tapered portions 25 may, alternatively, taper radially inward.

FIG. 2 further illustrates inner layer 20 extending along all or a portion of the inner surface 24 of stent 10. For example, FIG. 2 illustrates inner layer 20 extending along an inner surface of end portions 27, tapered portions 25 and medial portion 18. For purposes of the discussion herein, inner layer 20 may be interchangeably referred to as a liner, coating and/or covering. Liner 20 may extend circumferentially around the lumen of stent member 10. In other words, it can be appreciated that liner 20 may be defined as an annular layer that extends continuously around the lumen of stent member 10. Further, liner 20 may extend continuously (e.g., uninterrupted) around the lumen of stent 10, from the first end 21 to the second end 23.

As discussed above, FIG. 2 illustrates stent 10 may include an outer layer 22 disposed along an outer surface 26 of stent 10. For example, in some instances, stent 10 may include an outer layer 22 disposed along the outer surface of one or more of end portions 27.

In some instances (such as that illustrated in FIG. 2), outer layer 22 may be a continuous extension of inner layer 20. For example, FIG. 2 shows inner layer 20 extending along the inner surface 24 of end portions 27, whereby inner layer 20 "wraps" over the end 28 of the end portion 27 and continues to extend along the outer surface of end portion 27. It should be noted that, in this example, what has been described above as outer layer 22 may define the portion of the inner layer 20 which has "wrapped over" end 28 of tubular scaffold of stent 10 and further extends along the outer surface of end portion 27. Further, both the inner layer 20, and the portion of the inner layer 20 that wraps over end 28 of scaffold 10 to form outer layer 22 may, together, sandwich filaments 12 therebetween. Further, while FIG. 2 illustrates inner layer 20 wrapping around (e.g., extending continuously around) both end portions 27 of stent 10 in FIG. 2, it is contemplated that inner layer 20 may wrap around only one end portion 27 of stent member 10.

FIG. 2 illustrates that inner layer 20 may be fixedly attached to the inner surface of end portions 27 and/or tapered regions 25. In other words, FIG. 2 shows that inner layer 20 may be adhered (e.g., affixed, secured, etc.) to the inner surface of strut members 12 which define end portions 27 and/or tapered regions 25 of stent 10.

Additionally, FIG. 2 illustrates that, in some examples, a portion of inner layer 20 may be spaced away from (i.e., spaced radially inward of) the inner surface 24 of stent 10, providing a gap or space therebetween. In particular, FIG. 2 illustrates that the portion of inner layer 20 extending along the medial portion 18 of stent member 10 may be unattached to medial portion 18 of the tubular scaffold of stent 10 and spaced radially inward from the inner surface 24 of the tubular scaffold of stent 10. For example, FIG. 2 shows that liner 20 may be attached (e.g., circumferentially) at a first attachment point 30 and a second attachment point 32, with the length of liner 20 between attachment points 30/32 remaining unattached (i.e., not directly attached) to the tubular scaffold of medial portion 18 of stent 10. FIG. 2 shows that inner layer 20 may be unattached to the inner surface 24 of the tubular scaffold (i.e., the struts 12) of stent 10 along a portion of stent 10 between first attachment point 30 and second attachment point 32. It should be noted that the portion of stent 10 shown in FIG. 2 in which inner layer 20 is unattached to the inner surface 24 of struts 12 of stent 10 may correspond to the medial portion 18 of stent 10 described above. In other words, in some examples, inner layer 20 may be unattached and thereby extend radially inward from the inner surface 24 of the tubular scaffold (i.e., struts 12) along the medial portion 18 of stent 10.

As discussed above, stents that are designed to be positioned in a body lumen (e.g., esophageal or gastrointestinal tract) may have a tendency to migrate (due to peristalsis and/or the generally moist and inherently lubricious environment of the body lumens). Therefore, one method to reduce stent migration may include exposing tissue ingrowth promoting regions, such as uncovered and/or bare metal portions of the stent to the tissue of the body lumen. The uncovered or bare stent scaffold may provide a structure that promotes tissue ingrowth into the interstices or openings thereof. The tissue ingrowth may anchor the stent in place and reduce the risk of stent migration.

Accordingly, it can be appreciated that the portions of stent 10 discussed above which include an inner and/or outer layer which is attached (e.g., covers) stent struts or filaments 12 may act to prevent tissue from growing into the interstices or openings thereof. For example, the struts or filaments 12 of tapered regions 25 and end portions 27 of stent 10 which include inner layer 20 and/or outer layer 22 attached thereto to thereby span across interstices of the tubular scaffold may prevent tissue ingrowth along their respective surfaces and interstices therebetween.

However, it can be appreciated that tissue may be permitted to grow around, between, through, within, etc. those filaments 12 of stent 10 in which inner layer 20 is not attached (e.g., the portion of inner layer 20 extending along medial portion 18 of stent 10). In other words, FIG. 2 illustrates a "tissue ingrowth region" 36 defined along medial region 18 of stent 10. The detailed view of FIG. 2 illustrates that tissue ingrowth region 36 may be extend radially inward from the inner surface 24 of stent member 10 to the outer surface 38 of inner liner 20. The distance between the inner surface 24 of stent member 10 to the outer surface 38 of inner liner 20 may be depicted as "$D_1$" in FIG. 2. Distance "$D_1$" may be about 0.5 mm-10 mm, or about 1 mm-6 mm, or about 1.5 mm-4 mm, or about 2 mm.

FIG. 2 further illustrates that tissue ingrowth region 36 may be defined as the space between the inner surface 24 of the tubular scaffold of stent 10 and the outer surface 38 of liner 20 extending between attachment points 30/32. Tissue ingrowth region 36 may be positioned between attachment points 30/32. Thus, tissue ingrowth region 36 may be defined as a space between the inner surface 24 of the tubular wall defined by struts or filaments 12 of the stent 10 and the outer surface 38 of the wall of the inner layer 20 between the circumferential attachment points 30/32. Further, tissue ingrowth region 36 may be defined as extending circumferentially within the lumen of the tubular scaffold of stent 10. In other words, it can be appreciated that tissue ingrowth region 36 may be defined as an annular space that extends continuously around the lumen of the tubular scaffold formed by struts or filaments of stent 10 radially inward of the stent wall.

It can further be appreciated that liner 20 may be constructed from an elastic material in some instances. Accordingly, a liner 20 including an elastic material component may be able to stretch radially inward. For example, as tissue grows through the interstices of stent member 10, it may push radially inward against the outer surface 38 of inner layer 20. In response, inner layer 20 may deflect, stretch, etc. radially inward in response to inward forces (e.g., tissue ingrowth) acting thereupon. In particular, the space $D_1$ between the inner surface 24 of stent 10 and the outer surface 38 of liner 20 may increase as the liner 20 deflects radially inward. In other embodiments, the liner 20 may be inelastic and, therefore, may not deflect relative to stent 10.

While liner 20 may include an elastic element permitting it to deflect radially inward from the inner surface 24 of the tubular scaffold of stent 10, in some instances it may be desirable to limit the amount of deflection of inner layer 20. For example, FIG. 2 illustrates that inner layer 20 defines a lumen 40 extending therein. Lumen 40 may be designed to permit food and/or or other digestible material to flow therethrough. Therefore, in some instances it may be desirable to design inner layer 20 to preserve the passageway defined by lumen 40 to permit food and/or other digestible material to flow through stent 10 when implanted in a body lumen. In other words, it may be desirable in some instances to prevent lumen 40 from closing radially inward in on itself. In some instances the inner layer 20 may include reinforcing filaments (e.g., fibers) embedded in the material of the inner layer 20 that may be drawn taut after a threshold amount of stretching of the material of the inner layer 20 to prevent further stretching of the inner layer 20. In some instances, the reinforcement filaments may be arranged longitudinally, circumferentially, helically, randomly, or otherwise arranged in the inner layer 20.

FIG. 2 depicts an inner diameter of tubular scaffold of stent 10 along medial region 18 as "$D_4$." Further, FIG. 2 depicts an inner diameter of inner liner 20 along medial region 18 as "$D_2$." Diameter "$D_4$" may be about 10 mm-30 mm, or about 15 mm-25 mm, or about 20 mm, in some instances. Further, diameter "$D_2$" may be about 10 mm-30 mm, or about 15 mm-25 mm, or about 18 mm, in some instances. Additionally, in some instances, it may be desirable to design inner liner 20 such that the diameter "$D_2$" is greater than or equal to a given percentage of diameter "$D_4$." For example, in some instances diameter "$D_2$" may be greater than or equal to 10% of "$D_4$", or greater than or equal to 25% of "$D_4$", or greater than or equal to 50% of "$D_4$", or greater than or equal to 60% of "$D_4$", or greater than or equal to 75% of "$D_4$", or "$D_2$" may be between 10-20% of "$D_4$", or "$D_2$" may be between 20-30% of "$D_4$", or "$D_2$" may be between 30-40% of "$D_4$", or "$D_2$" may be between 40-50% of "$D_4$", or "$D_2$" may be between 50-75% of "$D_4$", or "$D_2$" may be between 75%-90% of "$D_4$", in some instances.

It can be appreciated that limiting the amount of deflection of inner liner 20 may not only assure that lumen 40 remains open, but it also limits that amount of tissue ingrowth occurring along stent 10. For example, by limiting the degree to which liner 20 may deflect radially inward along medial region 18, the amount of tissue ingrowth occurring along medial 18 may be controlled. As discussed above, controlling the amount of tissue ingrowth occurring along stent 10 may be desirable because the amount of tissue ingrowth may directly correspond to the force necessary to remove stent 10 from a body lumen. In other words, the stent 10 may be customized to have a given removal force by limiting the amount of elasticity (e.g., and thereby limiting the amount of radially inward deflection) of liner 20.

As can be appreciated from FIG. 2, end portions 27 may include an inner diameter depicted as "$D_3$." Diameter "$D_3$" may be greater than or equal to diameter "$D_2$." Diameter "$D_3$" may be about 15 mm-35 mm, or about 20 mm-30 mm, or about 25 mm, in some instances. In other words, inner layer 20 may be generally shaped to taper longitudinally from the end portion 27 closest to first end 21 to the medial portion 18. For example, the tapered portion 25 may bear some resemblance to a cone-shaped funnel. Further, as illustrated in FIG. 2, stent 10 may taper inwardly toward central longitudinal axis of stent 10 along flared portion 14 and may taper outwardly away from the central longitudinal axis of stent 10 along flared portion 16.

Figure 3:
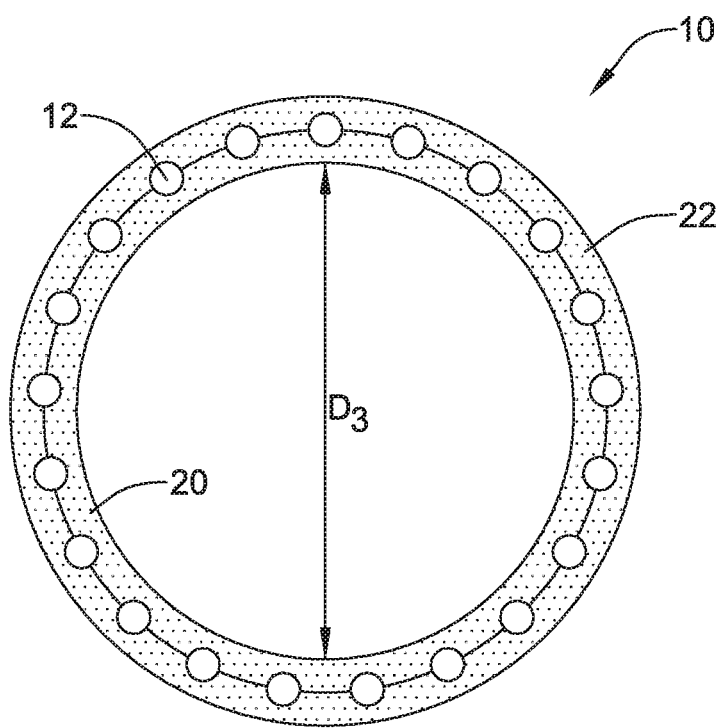
FIG. 3 is a cross-sectional view of the stent of FIG. 1 taken along line 3-3 of FIG. 2.

FIG. 3 illustrates a cross-section along line 3-3 of FIG. 2. As described above, this cross-section is taken through end portion 27 of flared region 14. As illustrated in FIG. 3, the filaments 12 of stent 10 defining end portion 27 may be sandwiched between inner layer 20 and outer layer 22. In other words, FIG. 3 illustrates that some portions of stent 10 (e.g., along flared region 14 and/or flared region 16), filaments 12 may have both inner layer 20 and outer layer 22 directly attached thereto. In other words, along some portions of stent 10 (e.g., along flared region 14 and/or flared region 16) no space may exist between filaments 12 and both inner layer 20 and outer layer 22.

Figure 4:
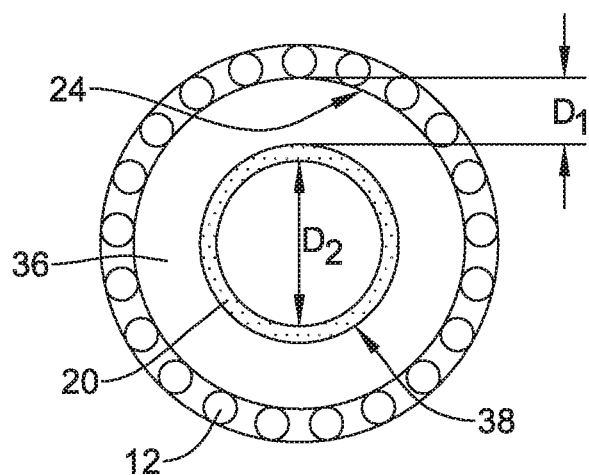
FIG. 4 is a cross-sectional view of the stent of FIG. 1 taken along line 4-4 of FIG. 2.

FIG. 4 illustrates a cross-section along line 4-4 of FIG. 2. As described above, this cross-section is taken through medial portion 18 of stent 10. As illustrated in FIG. 4, the inner layer 20 of stent 10 may be spaced away from (i.e., radially inward of) filaments 12 of stent 10 along medial portion 18. Further, FIG. 4 illustrates tissue ingrowth region 36 extending between the inner surface 24 of filaments 12 of stent 10 and the outwardly-facing surface 38 of inner member 20. Additionally, FIG. 4 illustrates tissue ingrowth region 36 extending circumferentially around the longitudinal axis of stent 10 radially outward of liner 20 and radially inward of filaments 12 of the tubular scaffold.

Figure 5:
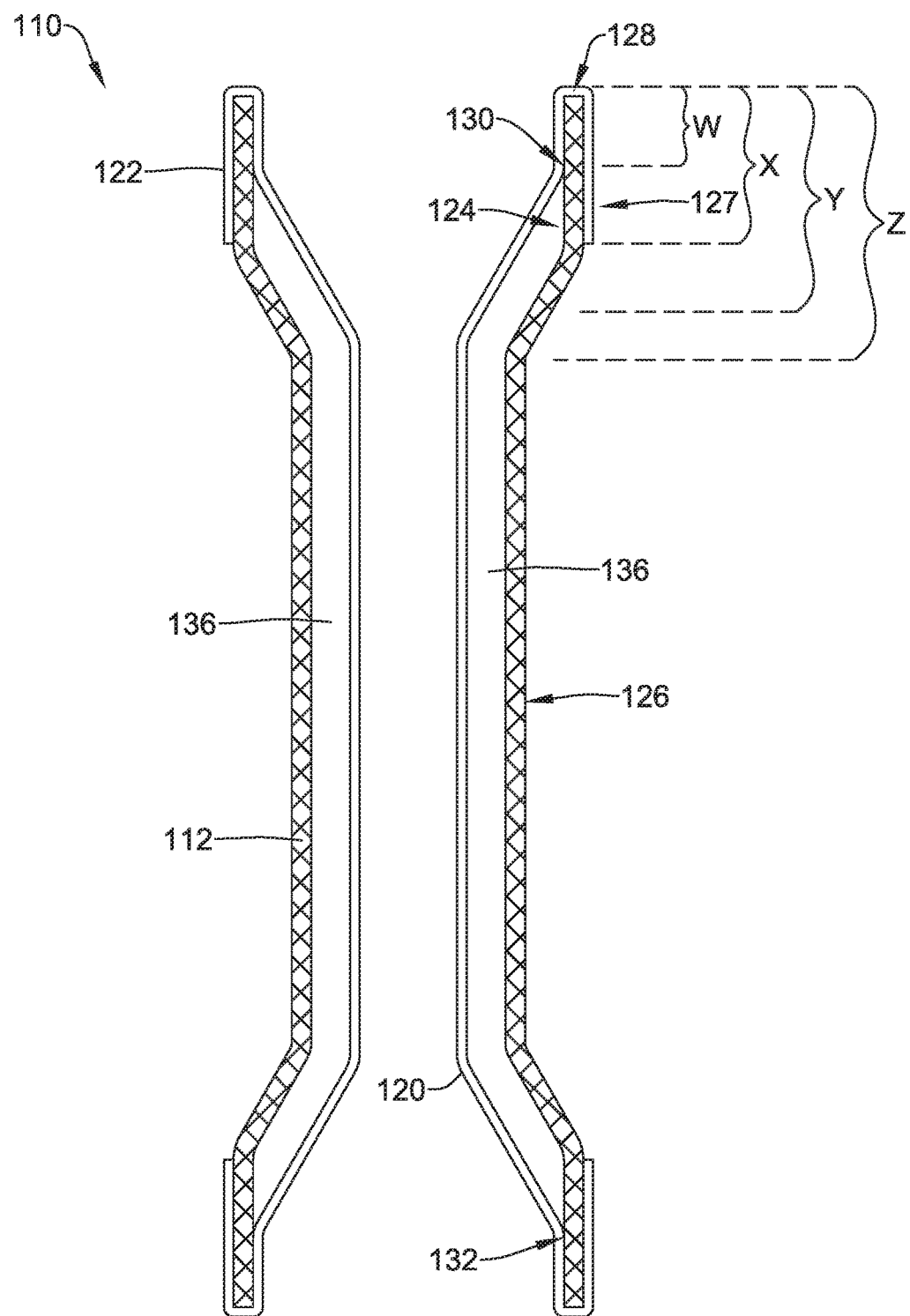
FIG. 5 is a cross-sectional view of the stent of FIG. 1 including a liner.

While the above discussion disclosed examples in which inner layer 20 and outer layer 22 are fixedly attached (e.g., directly secured) to the end portions 27 and/or tapered portions 25, other configurations are contemplated. For example, FIG. 5 illustrates an example stent member 110. Stent 110 may be similar in form and functionality to stent 10 described above. For example, stent 110 may include a liner 120 disposed within a lumen of the tubular scaffold of stent 110. Further, as illustrated in FIG. 5, liner 120 may be circumferentially attached along the inner surface 124 of stent 110 at attachment point 130 and/or attachment point 132. Attachment points 130/132 may be located at opposing end regions of stent 110, such as in opposing flared end regions of stent 110.

However, FIG. 5 illustrates that different attachment point locations 130/132 are contemplated along stent member 110. For simplicity purposes, example positions contemplated for attachment points 130/132 are depicted in terms of a distance from the end 128 of stent member 110. For example, the attachment points 130/132 are depicted as being a distance "W" (as measured along the outer surface 126 of stent 110) from end 128. In other examples, attachment points 130/132 may be positioned at distances depicted as "X," "Y" and "Z" (as measured longitudinally from end 128 of stent 110. Distance "Z" may be understood to be the equivalent attachment location of attachment points 30/32 along stent 110 described above. Additionally, in some examples distance "W" may be approximately 25% of distance "Z," distance "X" may be approximately 50% of distance "Z" and distance "Y" may be approximately 75% of distance "Z."

Additionally, it is contemplated that liner 120 may not be attached along the inner surface 124 of stent 110. For example, attachment points 130/132 may be located at the end point 128 of stent 110. Further, in instances where attachment points 130/132 are located at ends 128, liner 120 may cover and or encapsulate the ends 128 of stent 110.

It can be appreciated from FIG. 5 that the different attachment point 130/132 along stent 110 may correspond to different size tissue ingrowth regions 136 (described above as tissue ingrowth region 36 of stent 10). For example, the tissue ingrowth section 136 defined by attachment point 130/132 located a distance "W" from end 128 may be larger than a tissue ingrowth region 136 defined by attachment point 130/132 located a distance "Y" from end 128. For reasons discussed above, it can be appreciated that the larger tissue ingrowth regions may create a stent 110 which has increased removal forces.

Outer layer 122 may also extend any desired distance from end 128 of stent 110 along the outer surface of the tubular scaffold defined by filaments or struts 112. For example, outer layer 122 may extend a distance depicted as "W," "X," "Y" or "Z" from end 128. The distance outer layer 122 extends from end 128 of stent 110 may be the same or different than the distance for attachment points 130/132.

While the above discussion of stent 10 and stent 110 illustrates a variety of attachment locations along stent 10, it is contemplated that liner 20 may be attached at any location along the inner surface 24 and/or outer surface of stent member 10. The different attachment locations may result in stents having different performance characteristics (e.g., different removal forces, different anti-migration properties). It is noted that the attachment distances shown in FIG. 5 are equally applicable to the attachment point 132 at the opposite end of stent 110 and/or outer layer 122 at the opposite end of stent 110.

FIGS. 6A-8B illustrate example stents that may be similar in form and function to the stent designs disclosed above. For example, each of the stents shown in FIGS. 6A-8B may include an inner liner disposed within the lumen of the tubular scaffold of stent (e.g., as shown in FIG. 2). Further, each of the stents shown in FIGS. 6A-8B may also include an outer layer as described above (e.g., as shown in FIG. 1) extending along at least a portion of the flared end regions of the tubular scaffold. However, the stents illustrated in FIGS. 6A-8B may further include an additional outer layer (which could be formed separately or in conjunction with the outer layer disposed on the flared end regions and/or the inner layer) disposed along the outer surface of the medial portion of the stent, leaving a remainder of the tubular scaffold uncovered to promote tissue ingrowth therethrough.

Figure 6A:
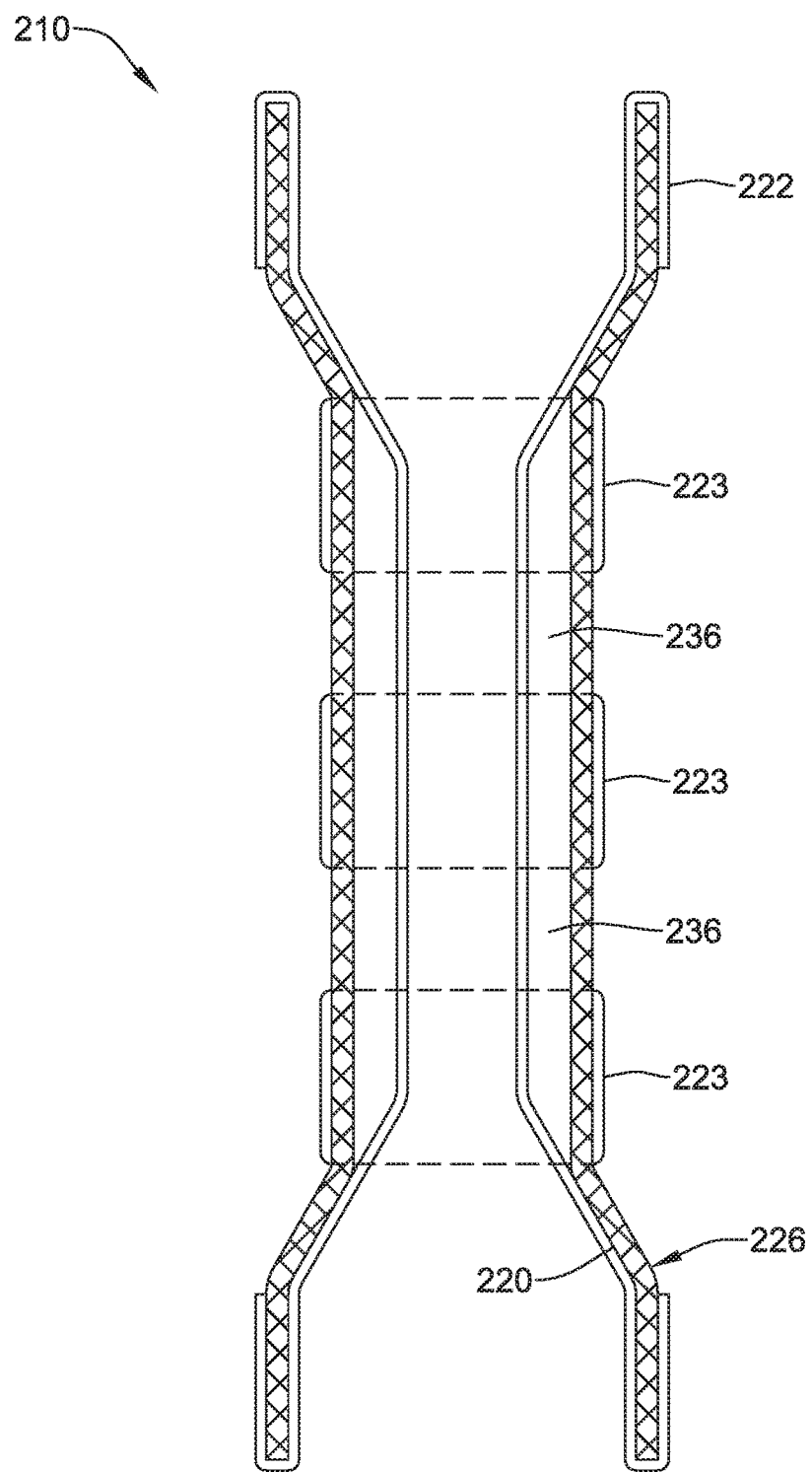
FIG. 6A is a cross-sectional view of another example stent including a liner and covered portions.
Figure 6B:
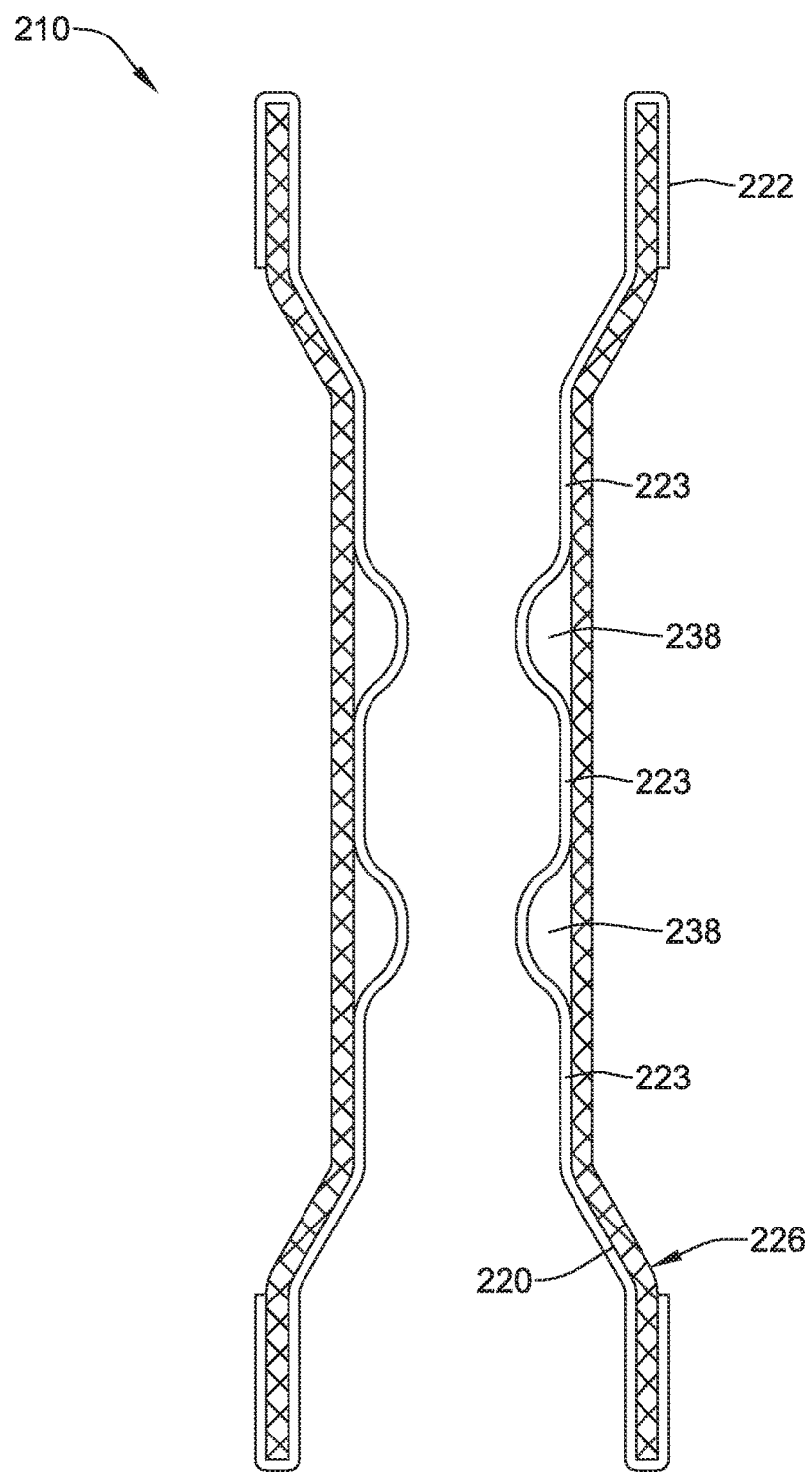
FIG. 6B is a cross-sectional view of another example stent including a liner and covered portions.
Figure 7A:
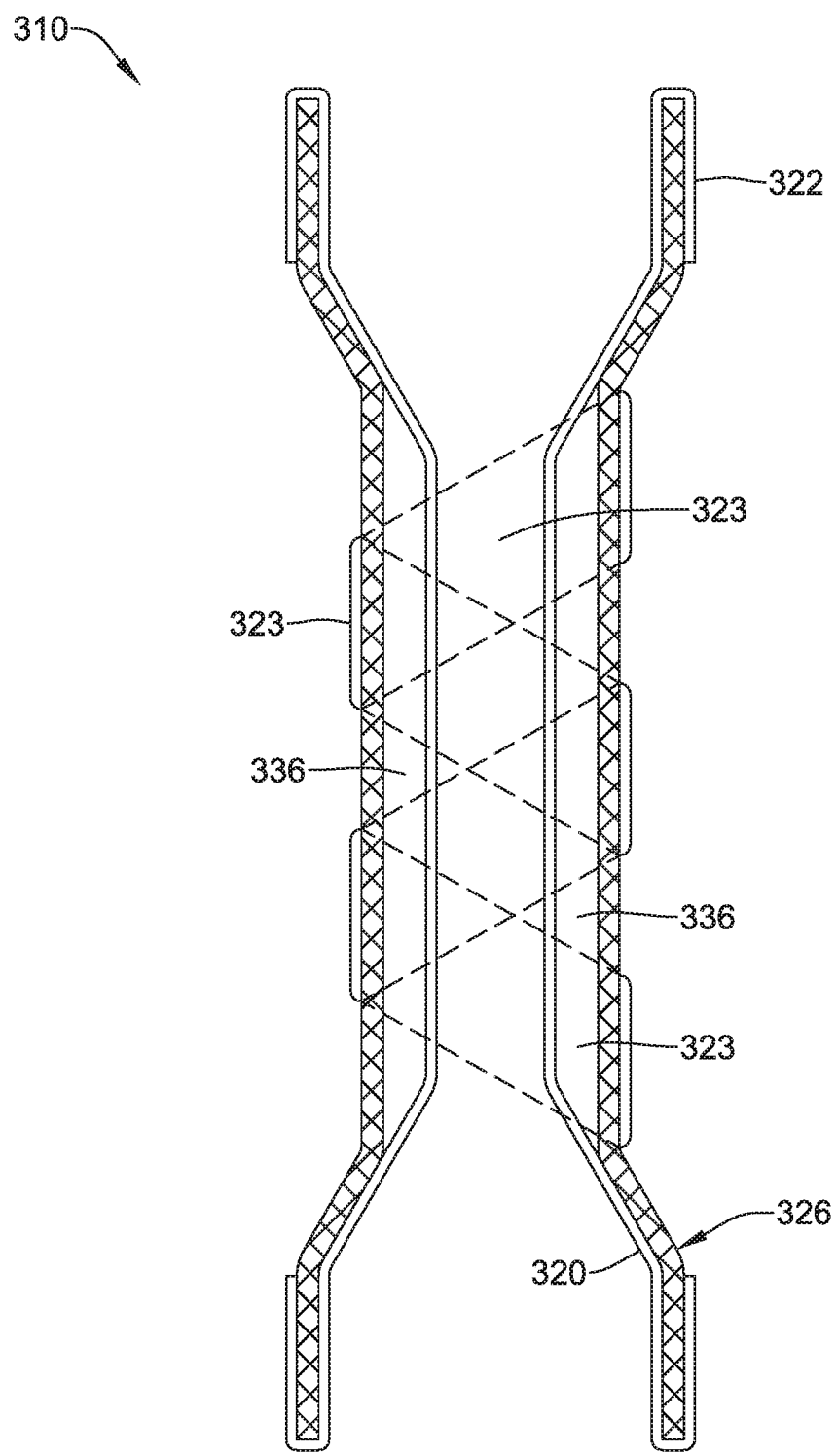
FIG. 7A is a cross-sectional view of another example stent including a liner and covered portions.
Figure 7B:
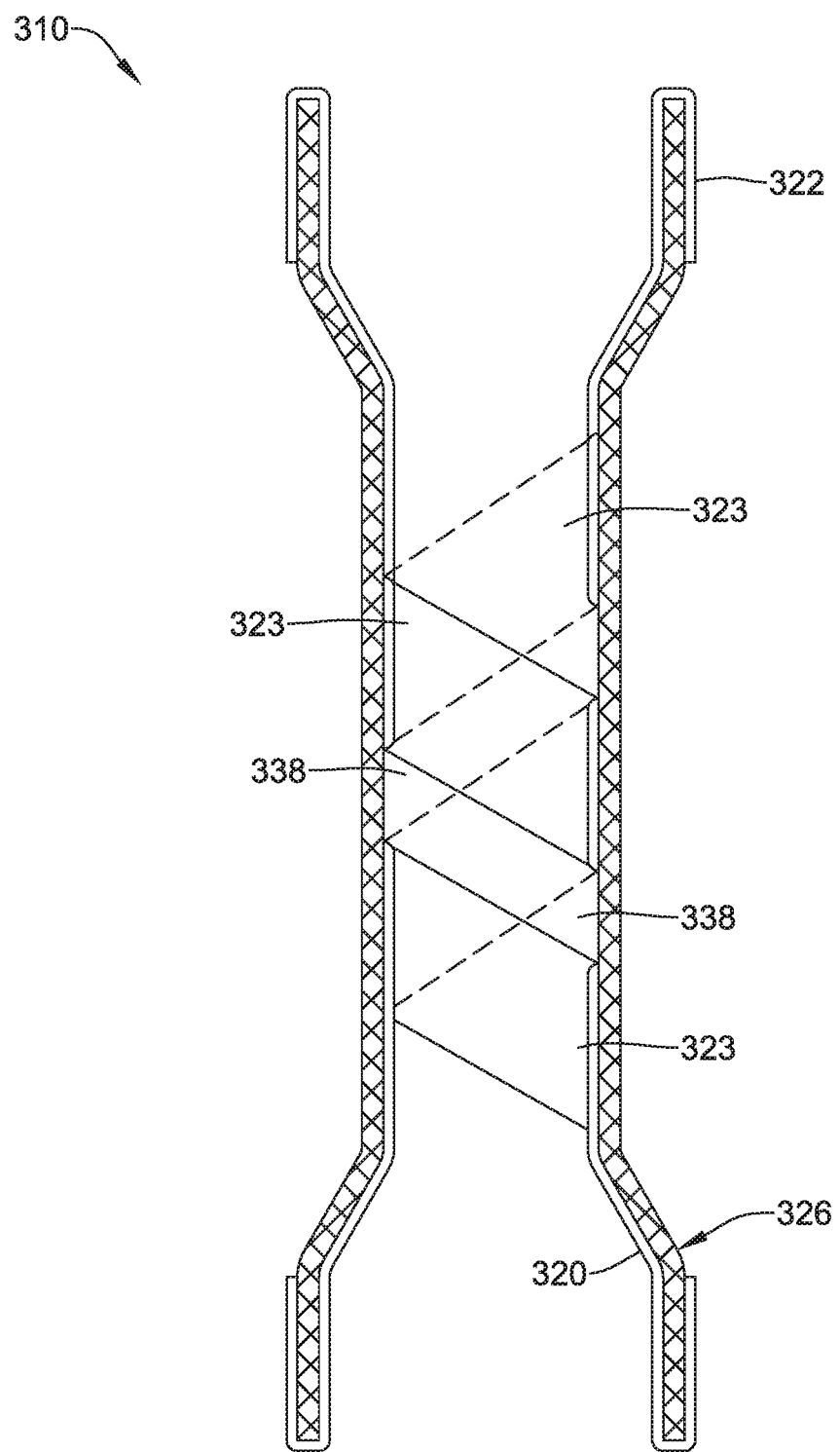
FIG. 7B is a cross-sectional view of another example stent including a liner and covered portions.

For example, FIG. 6A shows an example stent 210. Example stent 210 that may be similar in form and function to the stent designs disclosed above. However, as FIG. 6A illustrates, stent 210 includes additional outer layers 223 disposed along the outer surface 226 of the tubular scaffold of stent 210. FIG. 6A shows outer layers 223 as circumferential rings of material which may be positioned such that they extend circumferentially around the outer surface 226 of stent 210 (the dashed lines in FIG. 6A depict the outer layers 223 extending circumferentially around the outer surface 226 of stent 210) and spaced apart relative to one another. In some examples, outer layers 223 may be oriented such that they extend laterally across stent 210. As shown in FIG. 6A, individual outer layers 223 may be spaced longitudinally apart from one another. It can be appreciated that the configuration of outer layers 223 creates one or more tissue ingrowth regions 236 (similar to in function to those described above) along the medial region of stent 210. Tissue ingrowth regions 236 may be circumferentially uncovered portions of the tubular scaffold of stent 210. Inner layer 220 may be located radially inward of tissue ingrowth regions 236 to limit the amount a tissue ingrowth permitted.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. For example, FIG. 6B (which may be similar in form and function to the stent design disclosed above with respect to FIG. 6A) illustrates an alternative example stent having one or more portions of inner layer 220 extending along the inner surface 224 of stent 210 may be unattached to the inner surface of stent 210 and spaced radially inward from the inner surface 224 of the tubular stent 210 while other portions of the inner layer 220 are attached to the inner surface 224 of stent 210. The space created by the inner layer 220 extending radially inward of the inner surface 224 of the stent 210 may define one or more tissue ingrowth regions 236. Tissue ingrowth regions 236 may extend circumferentially around the inner surface 224 of stent 210.

FIG. 7 shows another example stent 310. Example stent 310 may be similar in form and function to the stent designs disclosed above. However, as FIG. 7 illustrates, stent 310 includes additional outer layer 323 disposed along the outer surface 326 of the tubular scaffold of stent 310. FIG. 7 shows outer layer 323 may be positioned such that it extends circumferentially around the outer surface 326 of stent 310 (the dashed lines in FIG. 7 depict outer layer 323 extending circumferentially around the outer surface 326 of stent 310). However, FIG. 7 shows that outer layer 323 may be oriented such it extends in a helical configuration around the outer surface 326 of stent 310. It can be appreciated that the configuration of outer layer 323 creates one or more tissue ingrowth regions 336 (similar in form and function to those described above) along stent 310. Tissue ingrowth regions 336 may be circumferentially uncovered portions of the tubular scaffold of stent 310. Inner layer 320 may be located radially inward of tissue ingrowth regions 336 to limit the amount a tissue ingrowth permitted.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. For example, FIG. 7B (which may be similar in form and function to the stent design disclosed above with respect to FIG. 7A) illustrates an alternative stent example having one or more portions of inner layer 320 may extend in a helical orientation along and attached to the inner surface 324 of stent 310. It can be appreciated that the helical configuration of inner layer 320 creates one or more tissue ingrowth regions 336 (similar in form and function to those described above) along stent 310. Tissue ingrowth regions 336 may be helically oriented uncovered portions of the tubular scaffold of stent 310.

Figure 8A:
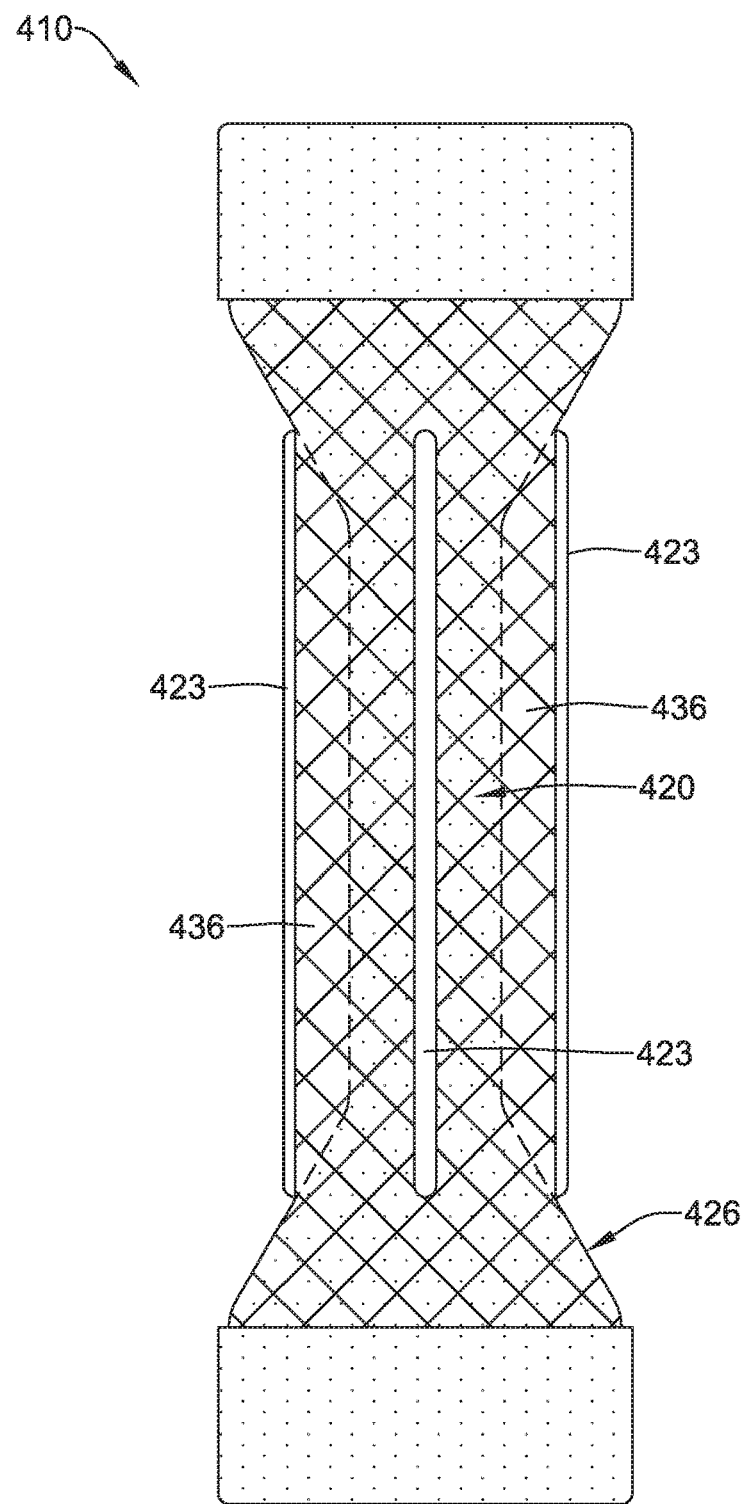
FIG. 8A is a plan view of another example stent including a liner and covered portions.

FIG. 8A shows an example stent 410. Example stent 410 that may be similar in form and function to the stent designs disclosed above. However, as FIG. 8A illustrates, stent 410 includes additional outer layers 423 disposed along the outer surface 426 of stent 410. FIG. 8A shows outer layers 423 may be positioned such that they extend longitudinally along the outer surface 426 of stent 410. As shown in FIG. 8A, individual outer layers 423 may be circumferentially spaced apart from one another. It can be appreciated that the configuration of outer layers 423 creates one or more tissue ingrowth regions 436 (similar to in function to those described above) along the stent 410. Tissue ingrowth regions 436 may be uncovered portions of the tubular scaffold of stent 410. Inner layer 420 may be located radially inward of tissue ingrowth regions 436 to limit the amount a tissue ingrowth permitted.

Figure 8B:
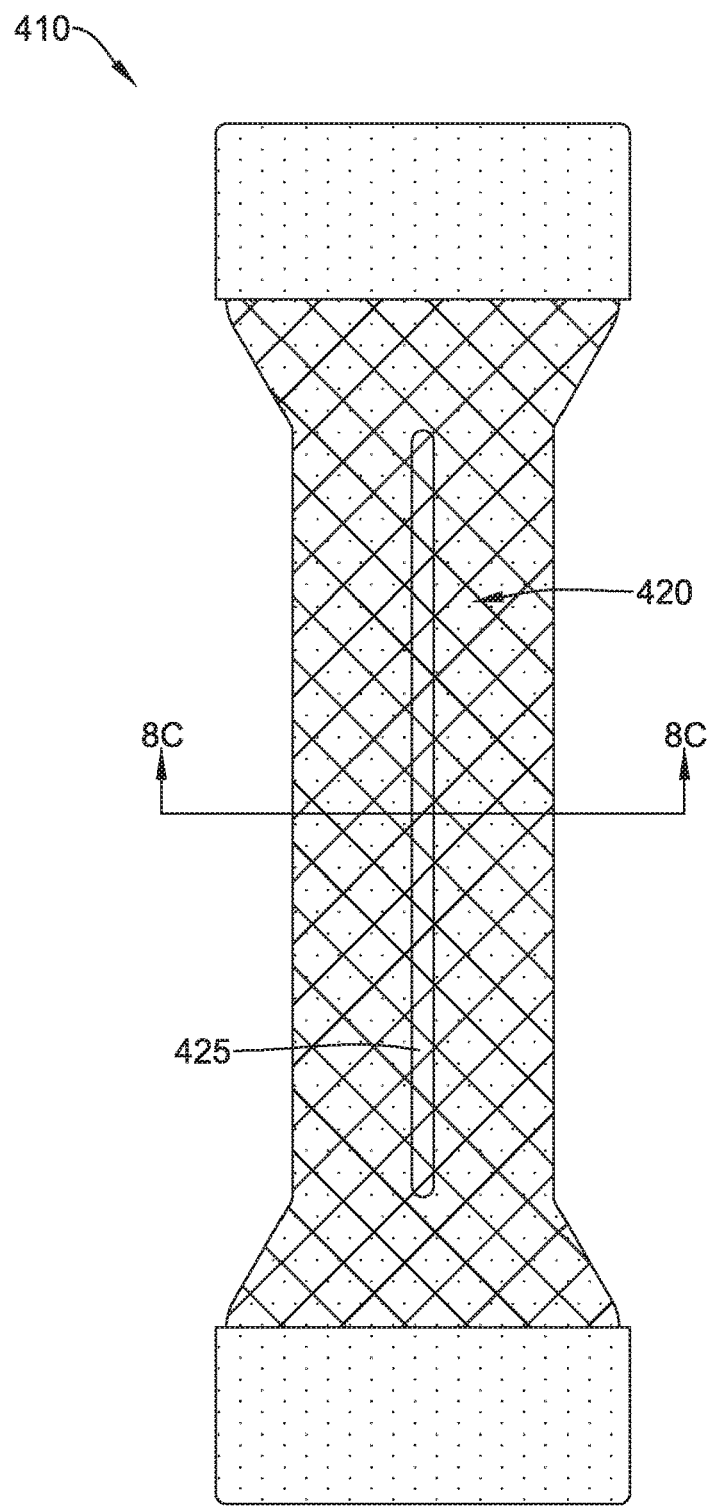
FIG. 8B is a plan view of another example stent including a liner.
Figure 8C:
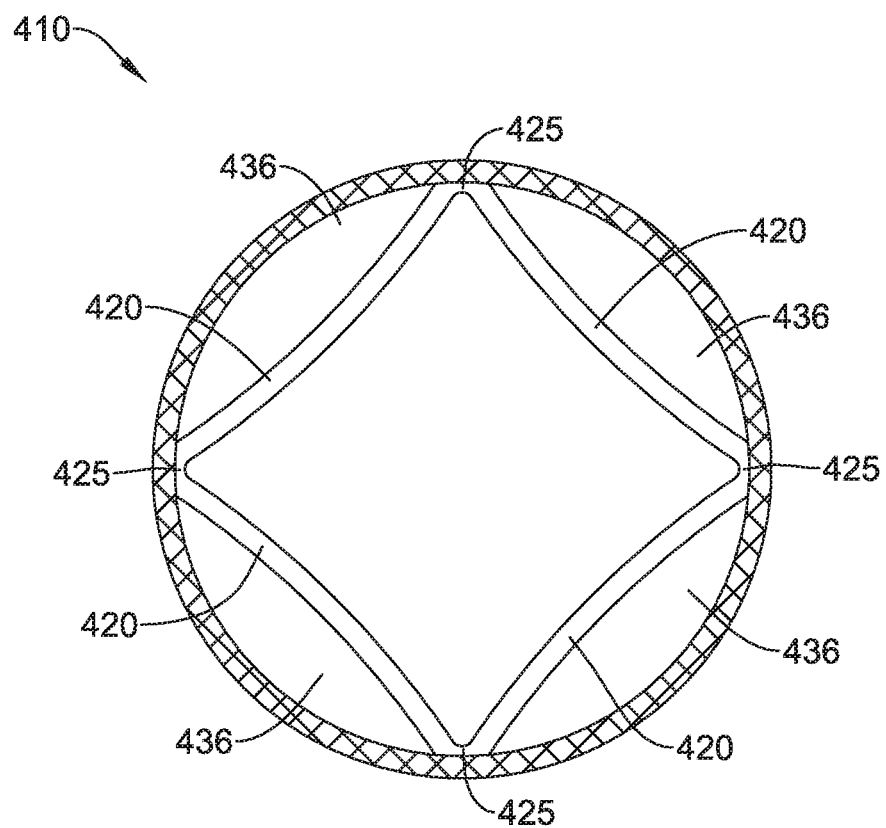
FIG. 8C is a cross-sectional view of another example stent.

Alternatively, some stent examples disclosed herein may be designed such that one or more portions of an inner layer extending along the inner surface of the stent may be spaced away from (i.e., spaced radially inward of) the inner surface of the stent, providing a gap or space therebetween. FIG. 8B illustrates an alternative stent example (which may be similar in form and function to the stent design disclosed above with respect to FIG. 8A) having an inner layer 420 spaced away from an inner surface of stent 410. As shown in FIG. 8B and FIG. 8C (discussed below), inner layer 420 may include one or more discrete attachment points 425 along the inner surface of stent 410 in which the inner layer 420 is attached to the inner surface of stent 410. It should be noted that the discrete attachment points of inner layer 420 may extend the full (or partial) longitudinal length (e.g., from the distal end region to the proximal end region) along the inner surface of stent 410.

FIG. 8C illustrates an example cross-section along line 8C-8C of example stent 410 shown in FIG. 8B. FIG. 8C illustrates that one or more portions of inner layer 420 may be attached along the inner surface of stent 410. Further, the inner layer 420 may be attached along the inner surface of stent 410 at one or more discrete attachment points 425. It can be appreciated that the space between the discrete attachment points 425 may create one or more tissue ingrowth regions 436.

Example stents disclosed herein may include one or more anchoring members designed to prevent the tubular member from shifting with respect to a body lumen in which the stent member is implanted. For example, some stents disclosed herein may include anti-migration elements. Anti-migration elements may include hooks, barbs, posts, flares, hoops, fins, quills, tines or the like. Anti-migration features may be beneficial in controlling the amount that a stent moves during and/or after deployment in the body lumen.

FIGS. 9-14 show example stents which may be similar in form and function to the stent designs disclosed above. For example, the stents in FIGS. 9-14 may be similar in form and function to the stent design shown in FIGS. 1 and 2.

Figure 9:
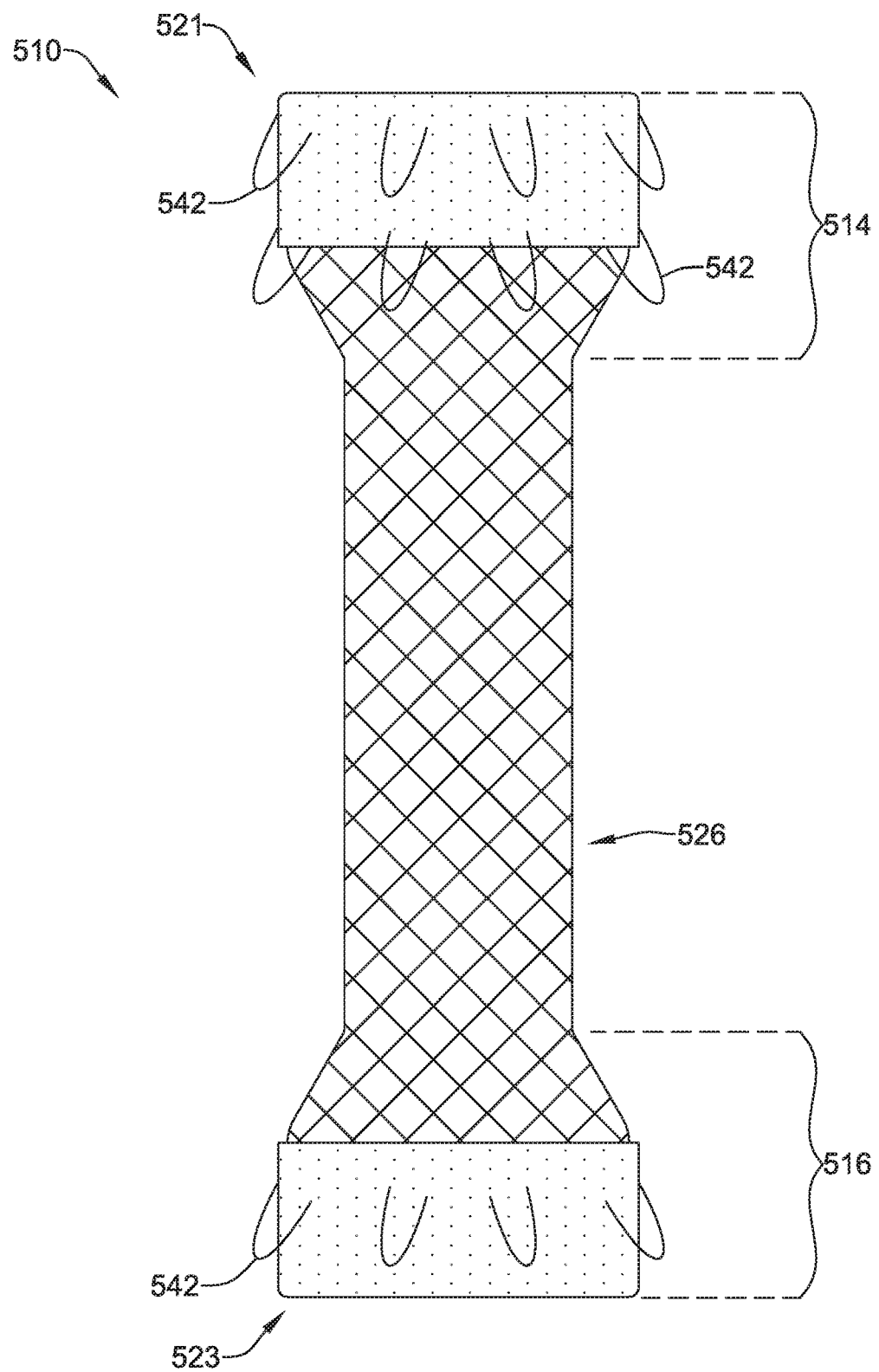
FIGS. 9-14 illustrate example stents including anchoring members.

FIG. 9 illustrates stent 510 including one or more anchoring members 542. The one or more anchoring members 542 may be positioned on and extend radially outward away from the outer surface 526 of stent 510 and be configured to contact an inner surface of the body lumen. For example, in at least some examples disclosed herein, anchoring members 542 may include a projection extending radially outward away from the outer surface of stent 510 to engage and/or penetrate into the wall of the body lumen. In some examples, anchoring members 542 may include a loop, barb, hook, point, spike, spur, rib, circumferential rim, prong, tines, etc.

FIG. 9 illustrates that anchoring members 542 may be positioned along different portions of the stent 510. For example, FIG. 9 shows anchoring members positioned along both flared region 514 and flared region 516. However, it is contemplated that anchoring members 542 may be positioned along only one of flared portions 514/516. Further, it is contemplated that anchoring members 542 may be positioned along any portion of the outer surface of stent 510 (including flared portion 514 and/or flared portion 516). For example, FIG. 9 shows two rows of anchoring members positioned along flared portion 514.

It is contemplated that anchoring members 542 may include separate components that are attached (e.g., welded) to the outer surface of stent 510. However, it is also contemplated that anchoring members 542 may be integrally formed from the filaments or struts of stent 510. For example, anchoring members 542 may be an extension of the knitted portion of stent 510. Additionally, it is contemplated that anchoring members 542 of stent 510 may extend away from stent 510 at a variety of angles, orientations, etc. For example, FIG. 9 shows anchoring members 542 located on flared region 514 and 516 pointing away from end 521 (e.g., toward end 523) of stent 510.

Other anchoring configurations and/or methods designed to prevent movement of example stents disclosed herein and the inner surface of a body lumen are contemplated in FIGS. 10-14. The example stents in FIGS. 10-14 may be similar in form and function to other stent designs disclosed herein.

Figure 10:
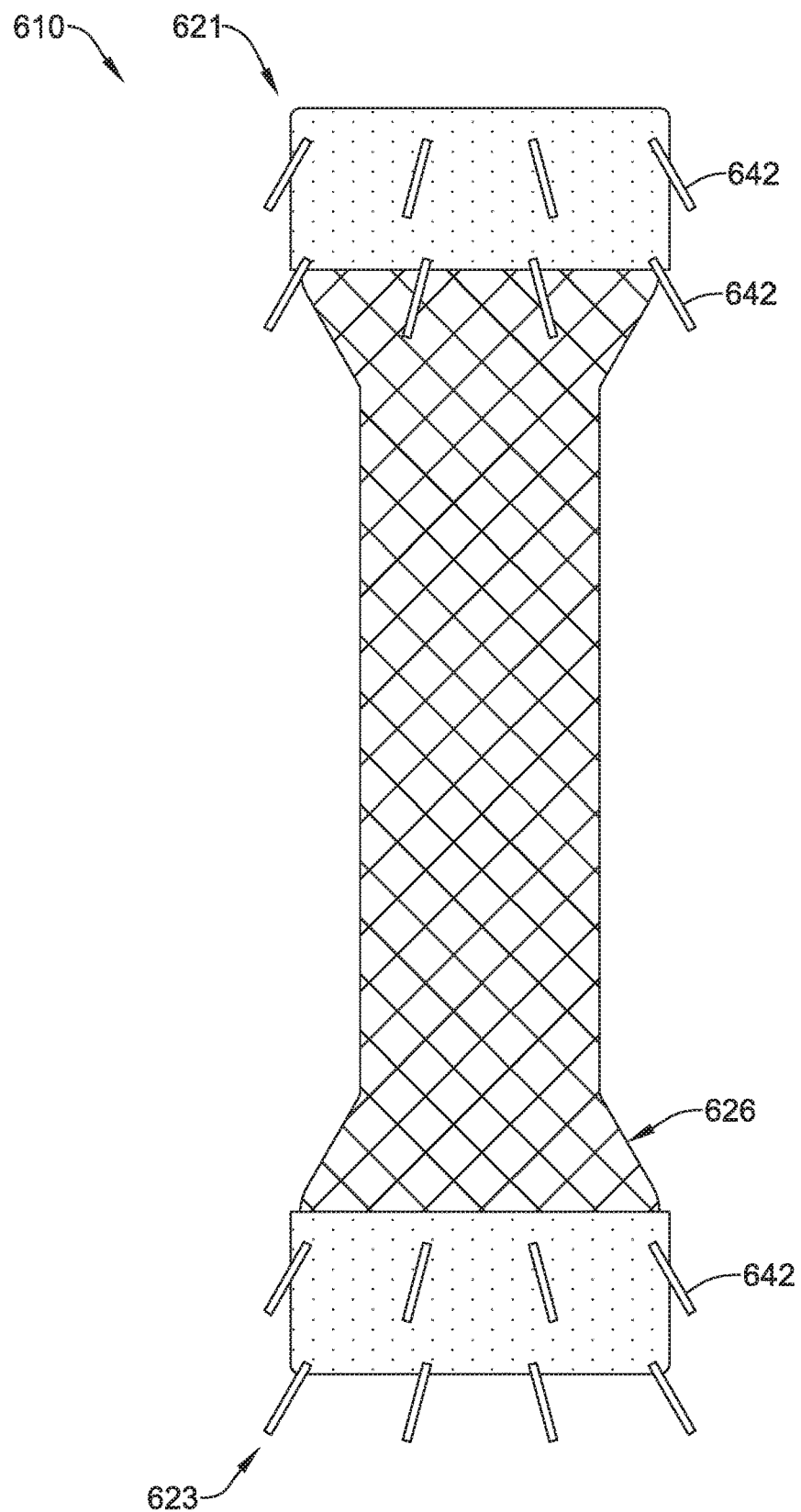

FIG. 10 shows stent 610 including anchoring members 642 which may resemble a post, quill or spike-like projection extending away from the outer surface 626 of stent 610. Additionally, anchoring members 642 are pointing away from end 621 (e.g., toward end 623) of stent 610.

Figure 11:
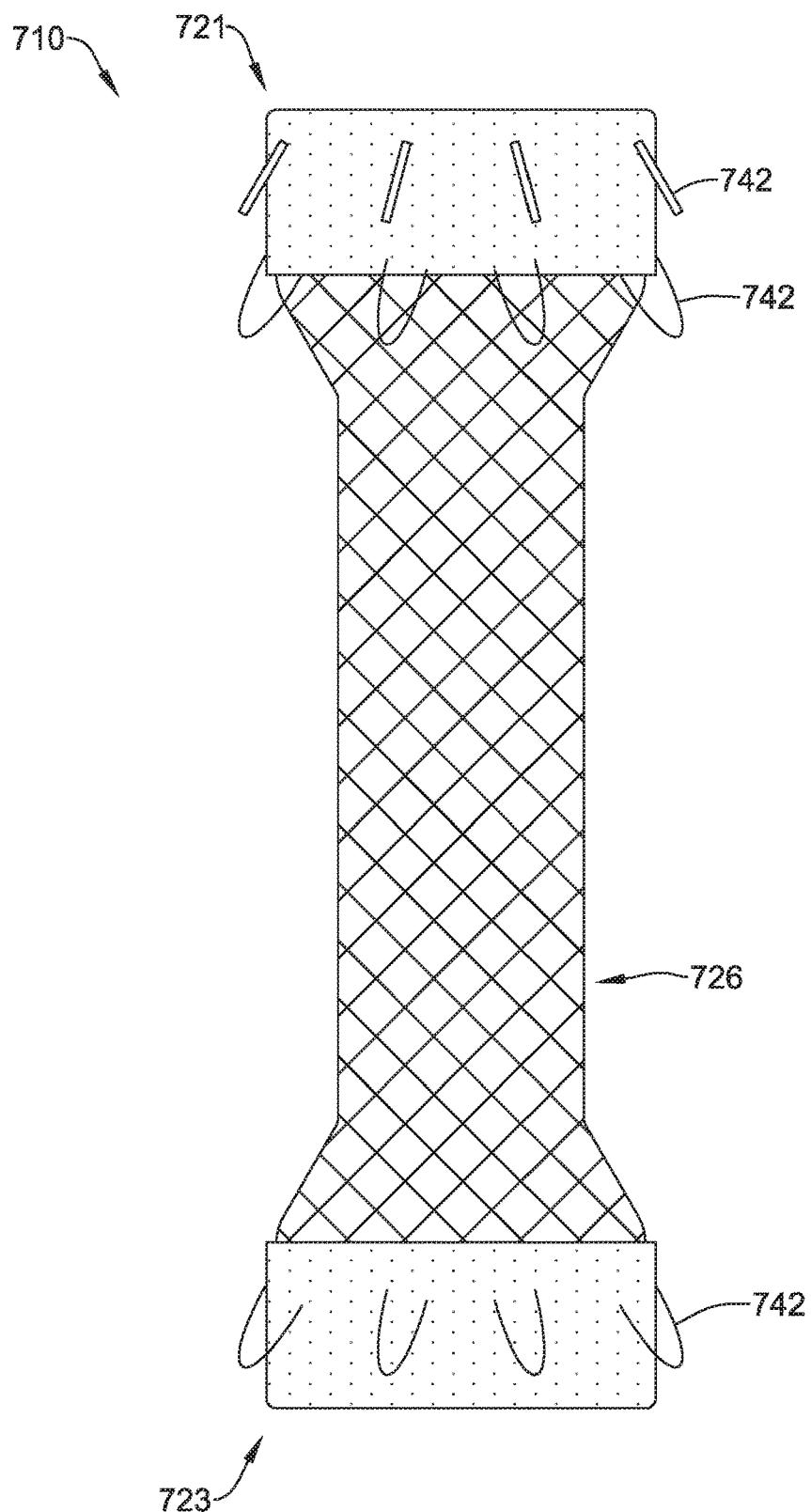

FIG. 11 shows stent 710 including anchoring members 742 which may include one or more loop-shaped and/or a post or spike-like projections extending away from the outer surface 726 of stent 710. Additionally, anchoring members 742 are pointing away from end 721 (e.g., toward end 723) of stent 710.

Figure 12:
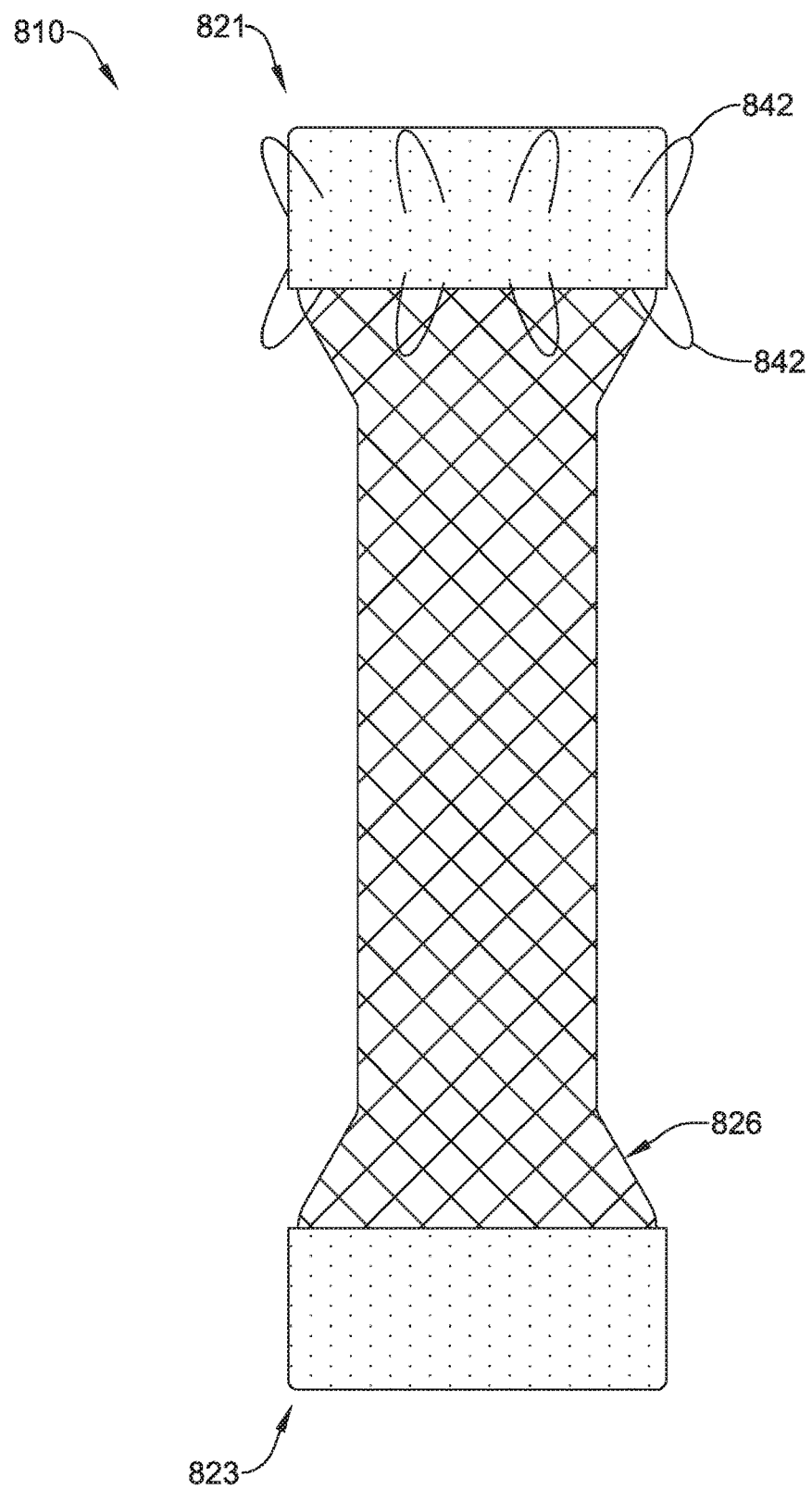

FIG. 12 shows stent 810 including anchoring members 842 which may include one or more loop-shaped projections extending away from the outer surface 826 of stent 810. Additionally, the flared end region of stent 810 may include some members 842 which are pointing away from end 821 of stent 810 and some members pointing toward end 823 of stent 810.

Figure 13:
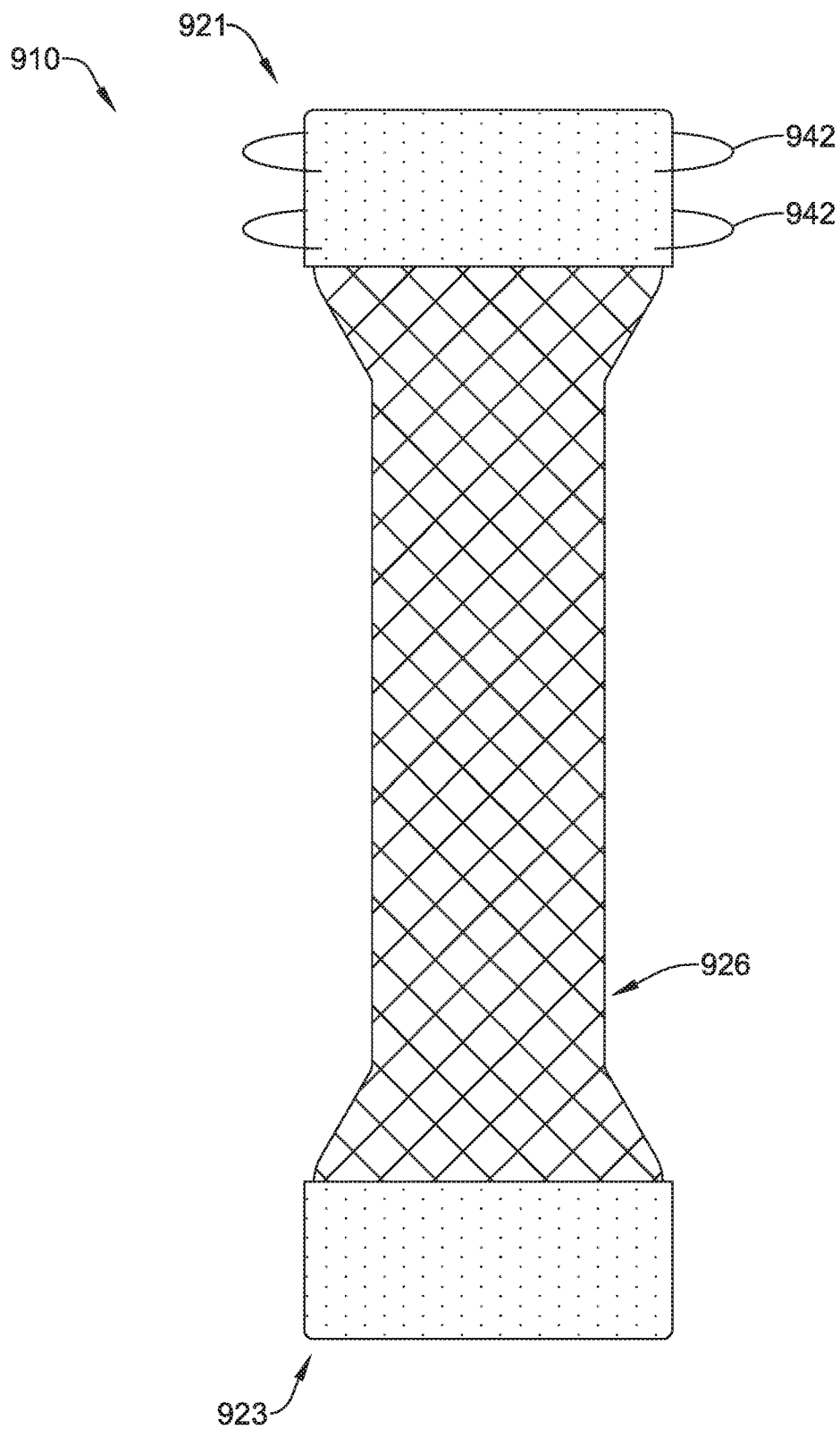

FIG. 13 shows stent 910 including anchoring members 942 which may resemble loop-shaped projections extending laterally away from the outer surface 926 of stent 910.

Figure 14:
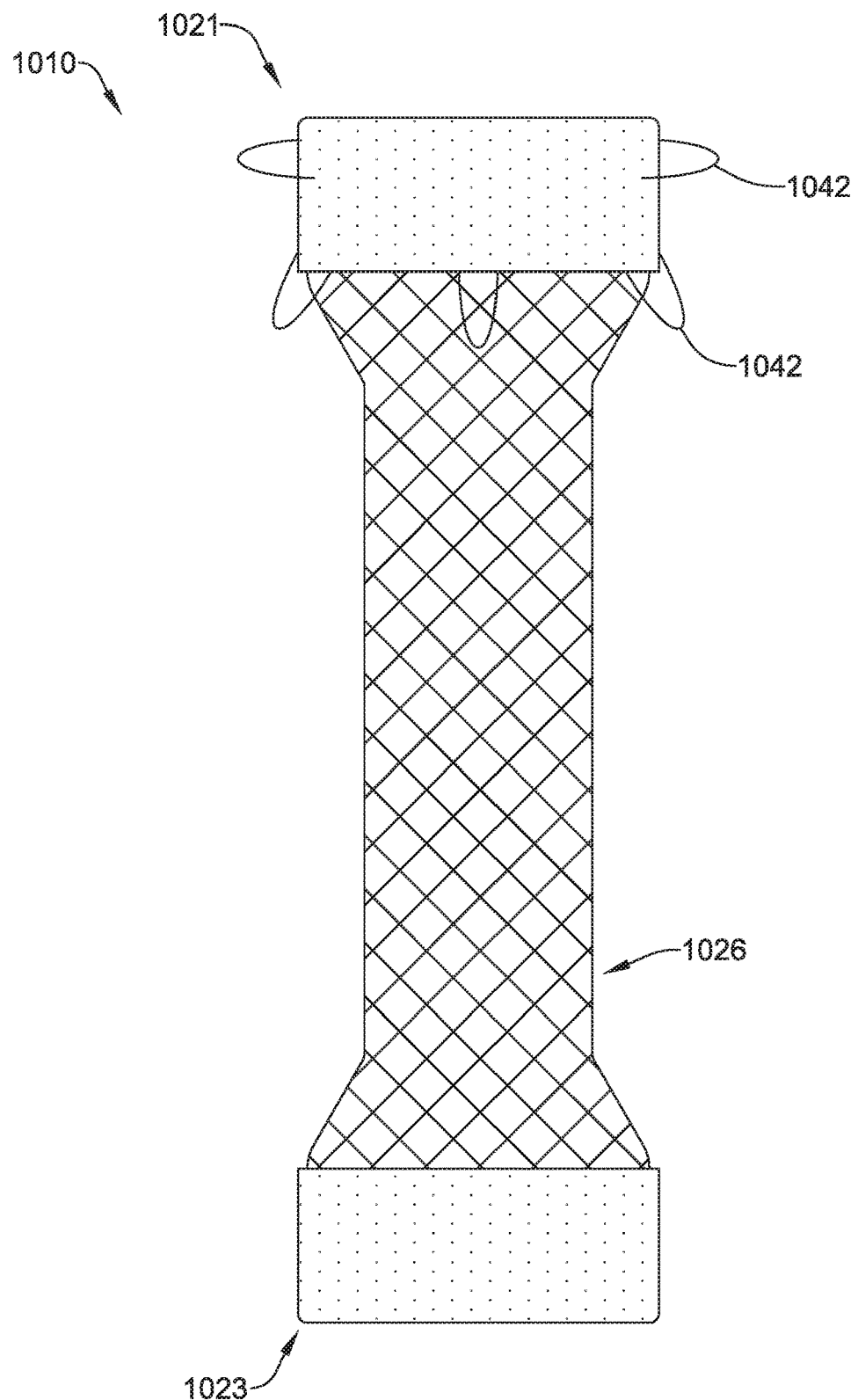

FIG. 14 shows stent 1010 having a flared end region including anchoring members 1042 which may include both laterally extending loop-shaped portions 1042 and also loop-shaped portions which are pointing away from end 1021 (e.g., toward end 1023) of stent 1010.

It can be appreciated that any of the anchoring members described above may be configured to prevent a stent from shifting longitudinally or migrating relative to an inner surface of a body lumen when the stent is positioned adjacent a target site. In some instances, the anchoring members that include a loop, barb, hook, point, spike, spur, rib, etc. may be configured to project into and/or through the wall of a body lumen, thereby affixing the anchoring member into the tissue of the body lumen and preventing the stent from longitudinally shifting or migrating with respect to the body lumen.

Figure 15A:
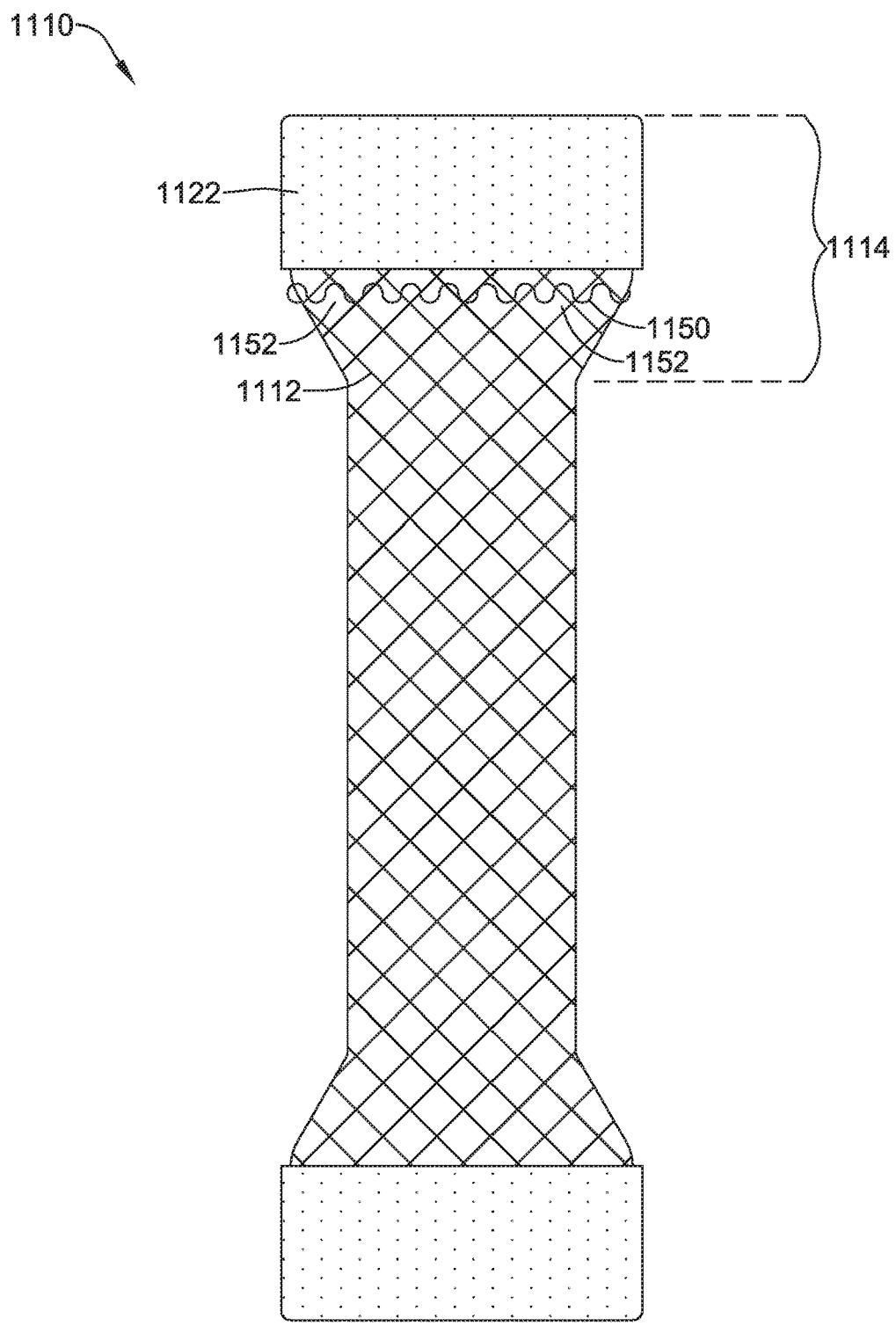
FIG. 15A is an example stent including a retrieval member.

FIG. 15 illustrates an example stent 1110 configured for removing implantable medical device 11 10 from a body lumen. Stent 1110 may be similar in form and function to other stent designs disclosed herein. As discussed herein, while medical device 1110 is implanted along a body lumen, tissue ingrowth may occur along the tissue ingrowth region, which may reduce migration of implantable medical device 1110 within the body lumen. However, in some examples, it may be necessary to remove medical device 1110 from the body lumen.

As shown in FIG. 15, stent 1110 may include a suture 1150 (e.g., filament) attached to the interstices 1152 formed from filaments 1112 of the flared region 1114 of stent 1110. In other words, suture 1150 may be interlaced among one or more interstices 1152 of filaments 1112 of stent 1110. Further, it can be seen in FIG. 15 that suture 1150 is positioned adjacent to the outer layer 1122. In other words, suture 1150 may be interlaced through interstices of 1152 of filaments 1112 circumferentially around an uncovered portion of the tubular scaffold of stent 1110 adjacent to outer layer 1122. In to order to remove stent member 1110, a clinician may grasp a portion of suture 1150 from adjacent the outer surface of the stent 1110. Grasping and pulling suture 1150 may cinch down a portion of stent 1110, causing stent 1110 to collapse radially inward, thereby releasing from the body lumen. Further, it is contemplated that, in at least some examples, suture 1150 may include a longer trailing portion (not shown) configured to be easily grasped by a removal device.

Figure 15B:
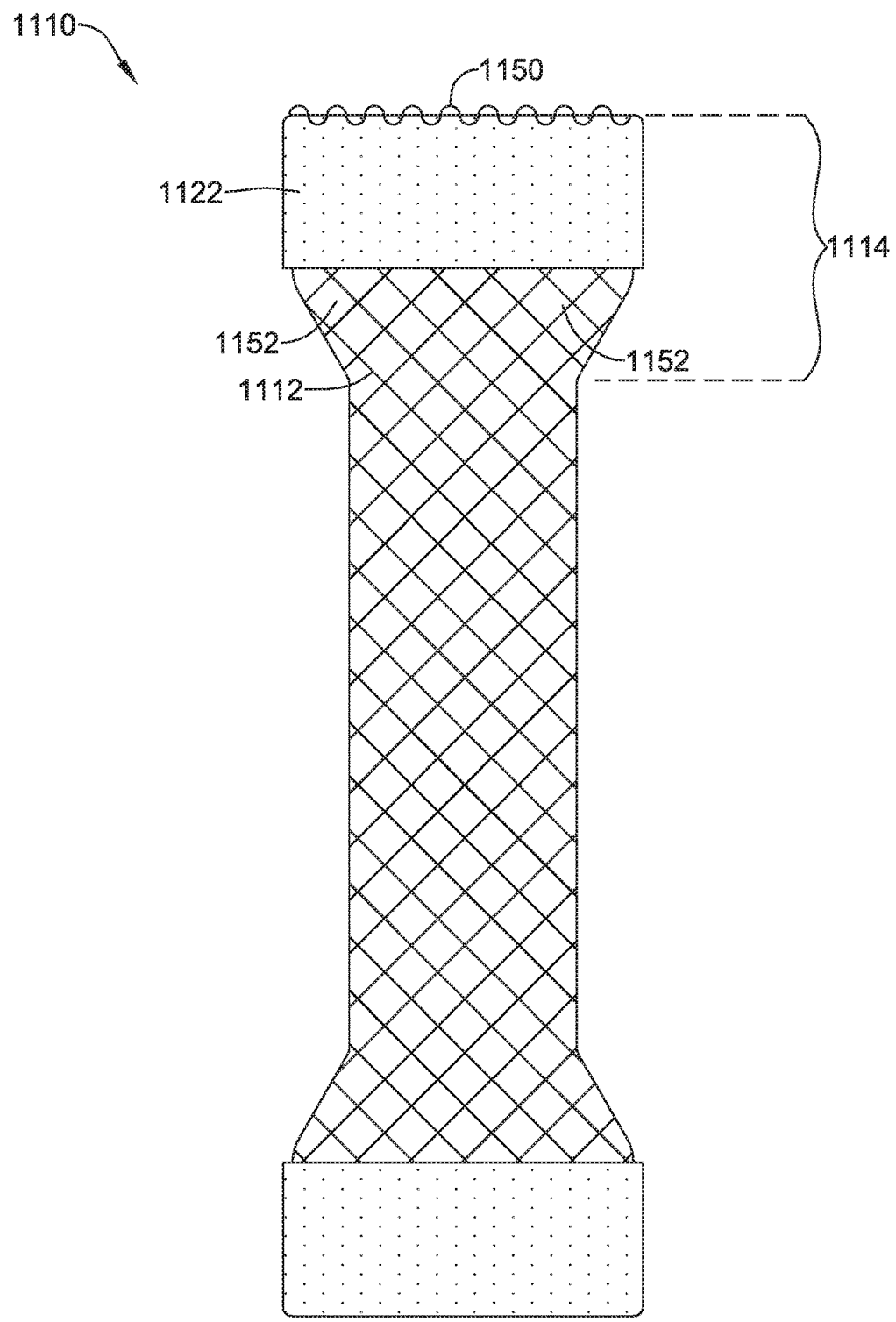
FIG. 15B is an example stent including a retrieval member.

Additionally, FIG. 15B illustrates the example stent 1110 described above with respect to FIG. 15A. However, as illustrated in FIG. 15B, the suture 1150 may be positioned adjacent to the end portion 1128 of stent 1110. Similar to that described above with respect to FIG. 15A, suture 1150 may be interlaced through outer layer 1122 and/or interstices of 1152 of filaments 1112. Further, suture 1150 may extend circumferentially around the tubular scaffold of stent 1110. In order to remove stent member 1110, a clinician may grasp a portion of suture 1150 from adjacent the outer surface of the stent 1110. Grasping and pulling suture 1150 may cinch down a portion of stent 1110, causing stent 1110 to collapse radially inward, thereby releasing from the body lumen. Further, it is contemplated that, in at least some examples, suture 1150 may include a longer trailing portion (not shown) configured to be easily grasped by a removal device.

In some instances, it may be desirable to attach and/or couple a secondary treatment device to one or more of the example stent designs disclosed herein. For example, in some instances it may be desirable to deploy a stent in a body lumen, wait for a hyperplastic response to occur (e.g., for tissue ingrowth to occur) such that the tissue ingrowth affixes the stent to the body lumen, and then deploy and/or attach a secondary treatment device to the stent. As will be illustrated below, a variety of secondary treatment devices may be contemplated for attachment to an example stent. In some examples, the secondary treatment devices may be similar in form and function to the stent designs disclosed herein. However, in other instances, the treatment devices may be different (e.g., include a variety of different coupling mechanisms, geometries, etc.) from the stents described herein.

Figure 16:
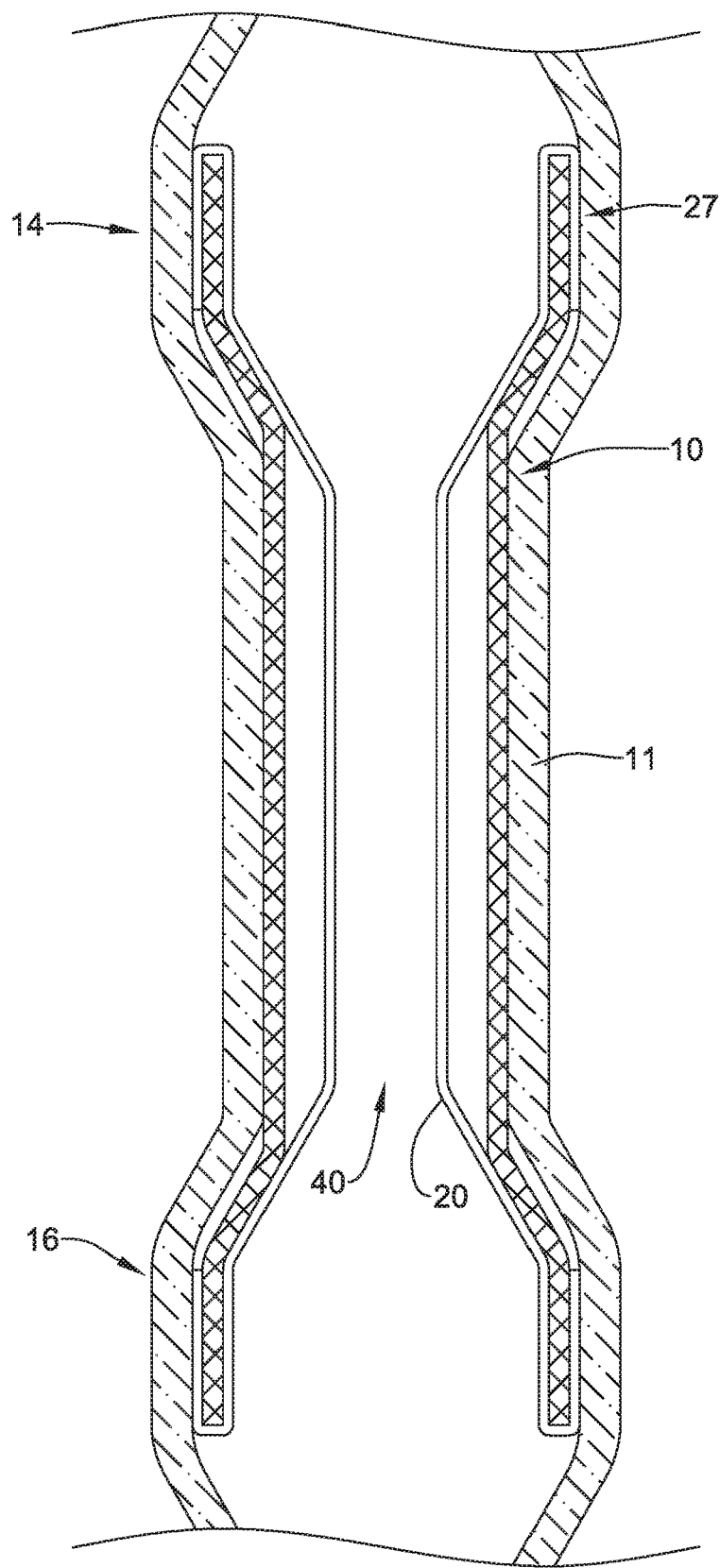
FIGS. 16-18 illustrate an example stent positioned in a body lumen.
Figure 17:
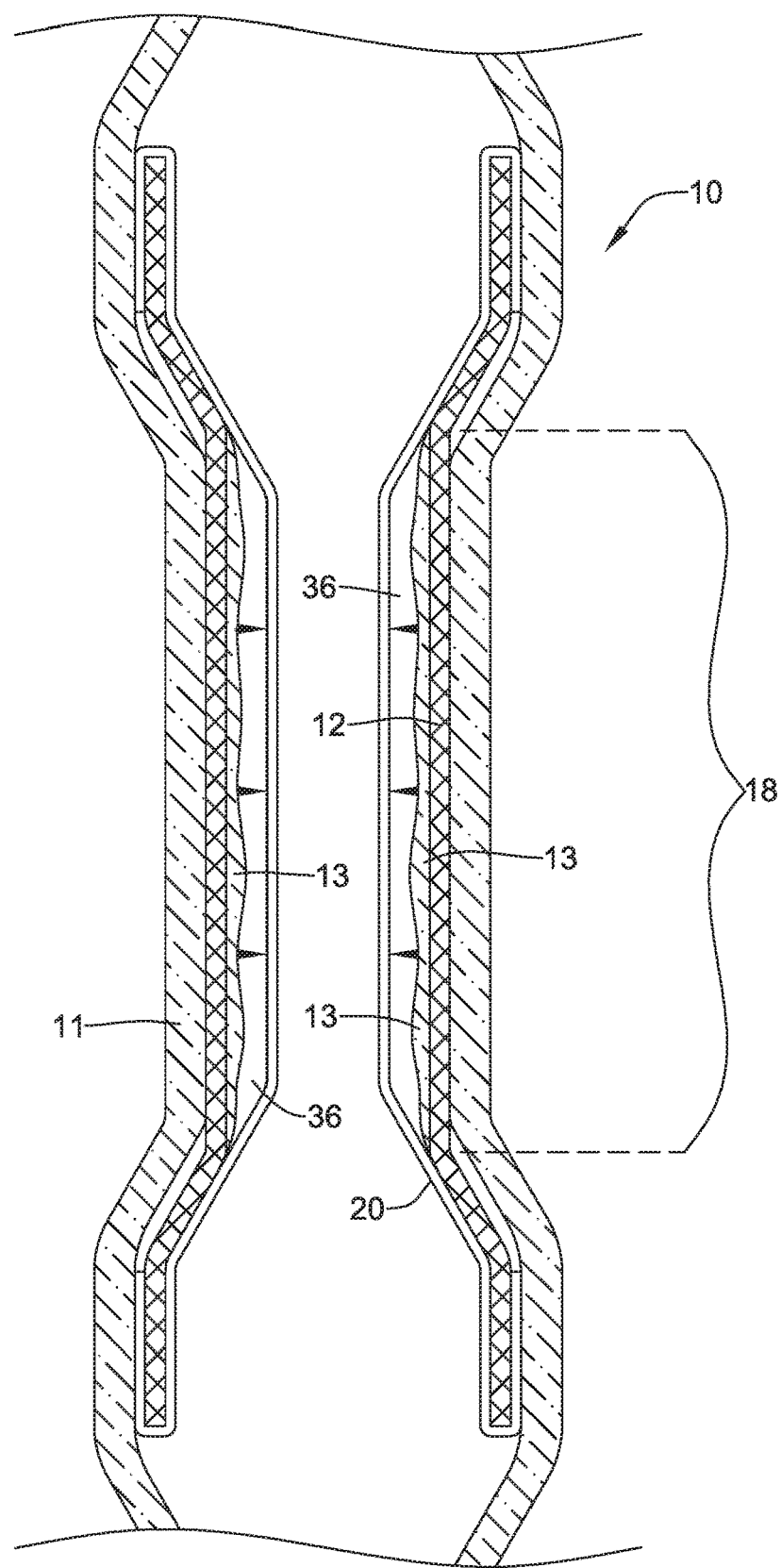
Figure 18:
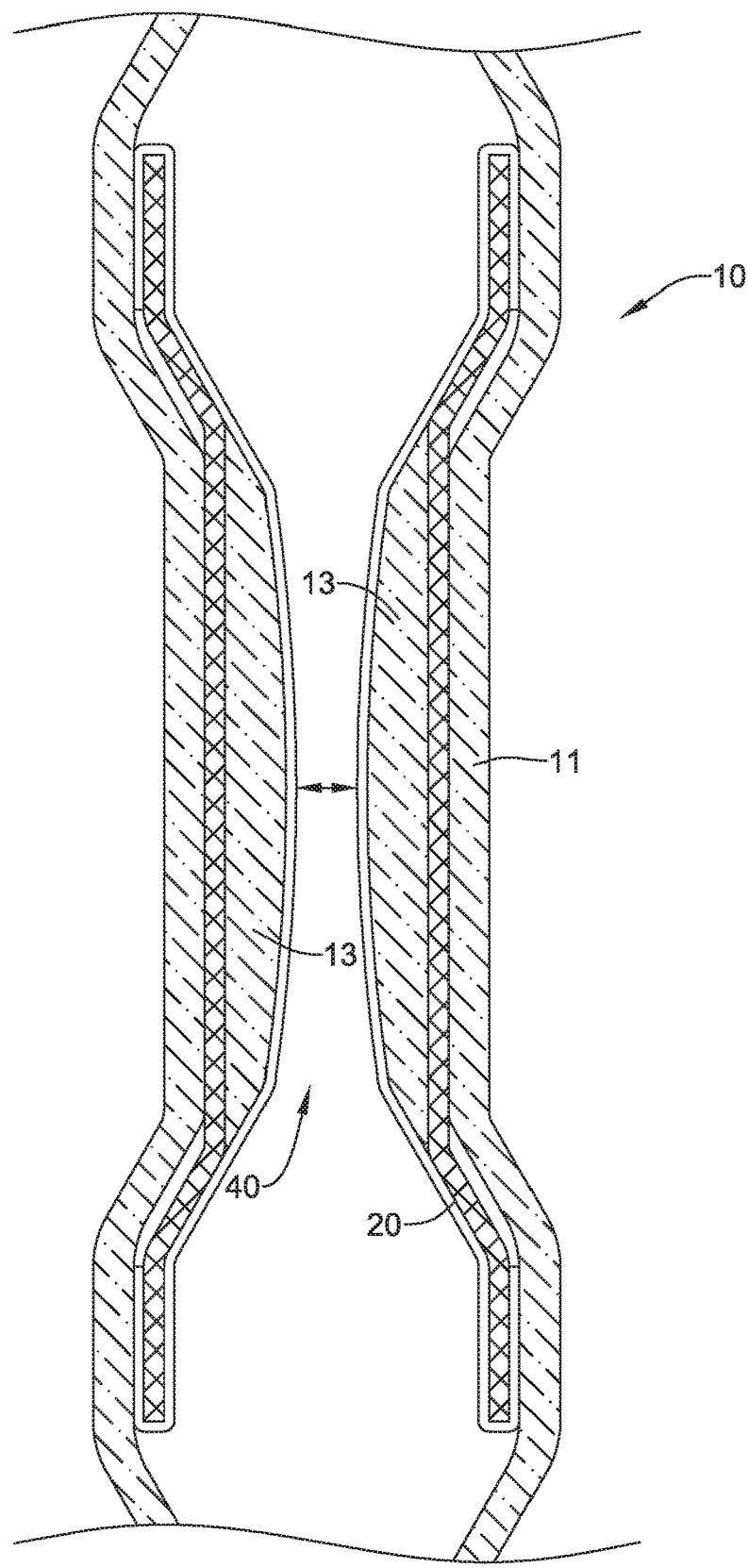

FIGS. 16-18 illustrate an example stent undergoing a hyperplastic response of tissue within an example body lumen. FIG. 16 shows example stent 10 deployed in body lumen 11. As illustrated, upon initial deployment in the body lumen 11, the end portion 27 of the first flared region 14 and the end portion 27 of the second flared region 16 may apply a radially outward force upon the inner surface of body lumen 11 as the expandable scaffold of stent 10 expands to an expanded state in the body lumen 11. This radially outward force exerted on the inner surface of body lumen 11 may provide a temporary resistance to migration of stent 10 within the body lumen 11.

Additionally, the end portions 27 of stent 10 may contact the tissue on the inner surface of body lumen 11. This contact of the end portions 27 with the tissue of the inner surface of the body lumen 11 may provide a seal that funnels food or other material through lumen 40 of stent 10. For example, as food or other material travels down the esophagus, the flared portions 14/16 of stent 10 may prevent the food from traveling along the exterior of stent 10 and along the inner surface of body lumen 11. Rather, flared portions 14/16 are designed to provide a circumferential seal around the inner surface of body lumen 11 such that the food is directed through the lumen 40 of stent 10. As discussed above, the inner layer 20 of stent 10 may create a passageway (e.g., lumen 40) through which food and other material may travel (without leaking to the outer surface of stent 10).

FIG. 17 illustrates tissue 13 extending through the stent filaments 12 along the medial region 18 of stent member 10 radially inward of the uncovered portion of the tubular scaffold of stent 10. FIG. 17 further illustrates that the tissue 13 is growing into the tissue ingrowth region 36 toward liner 20 (as depicted by the arrows in FIG. 17). Thus, tissue may grow through interstices of the tubular scaffold of stent 10 and around struts or filaments 12 of tubular scaffold of stent 10 throughout the uncovered portion of medial region 18.

FIG. 18 illustrates that tissue 13 has grown radially inward from the wall of example body lumen 11 to a position in which it has contacted inner layer 20 radially inward. However, as shown in FIG. 18, inner layer 20 has reached a point at which it will no longer deflect radially inward, and therefore prevents tissue 13 from further collapsing lumen 40 of stent member 10 (as depicted by the double-ended arrow in FIG. 18).

FIGS. 19-22 illustrate an example methodology for deploying example stent (or any other devices disclosed herein) into a body lumen (e.g., the esophagus). While the following figures describe example stent 10 being deployed in the esophagus, it is contemplated that the methodology may be used to deploy stent 10 (or any other devices disclosed herein) into any other body lumen. For illustrative purposes, stent 10 described in the following methodology may be similar in form and function to stent 10 of FIGS. 1 and 2 discussed above.

Figure 19:
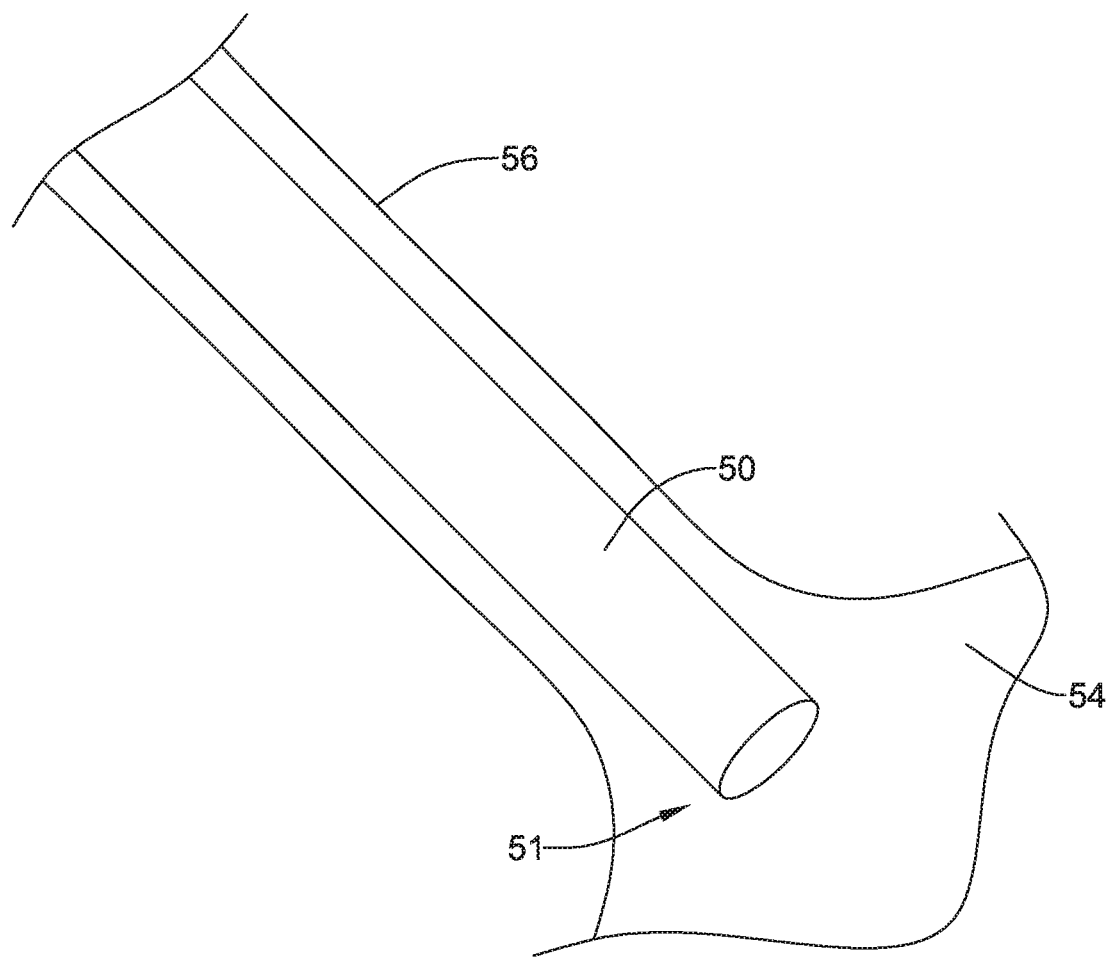
FIGS. 19-22 illustrate an example method for deploying an example stent in an esophagus.

FIG. 19 shows an example first step in deploying a stent 10 into the esophagus 56. Specifically, a first end portion 51 of delivery device 50 may be advanced through the esophagus 56 such that first end portion 51 may be positioned into the stomach 54.

Figure 20:
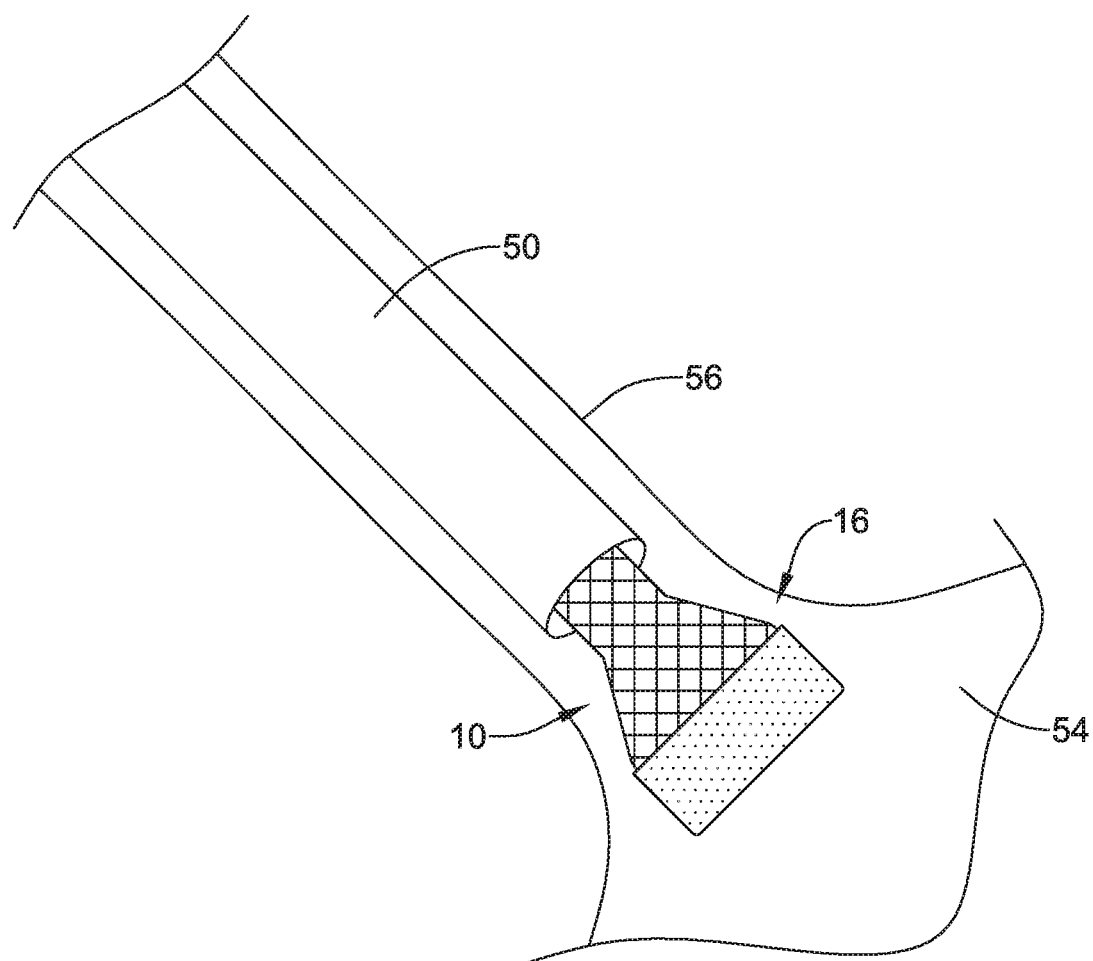

FIG. 20 illustrates an example second step in deploying stent 10 into the esophagus 56. Specifically, FIG. 20 illustrates that a clinician may initially deploy the second or distal flared portion 16 of stent 10 into the stomach 54. It can be appreciated that the stomach 54 may provide enough open area for flared portion 16 of stent 10 to completely expand. In other words, flared portion 16 may expand to its full radial extent before being positioned within the esophagus 56.

Figure 21:
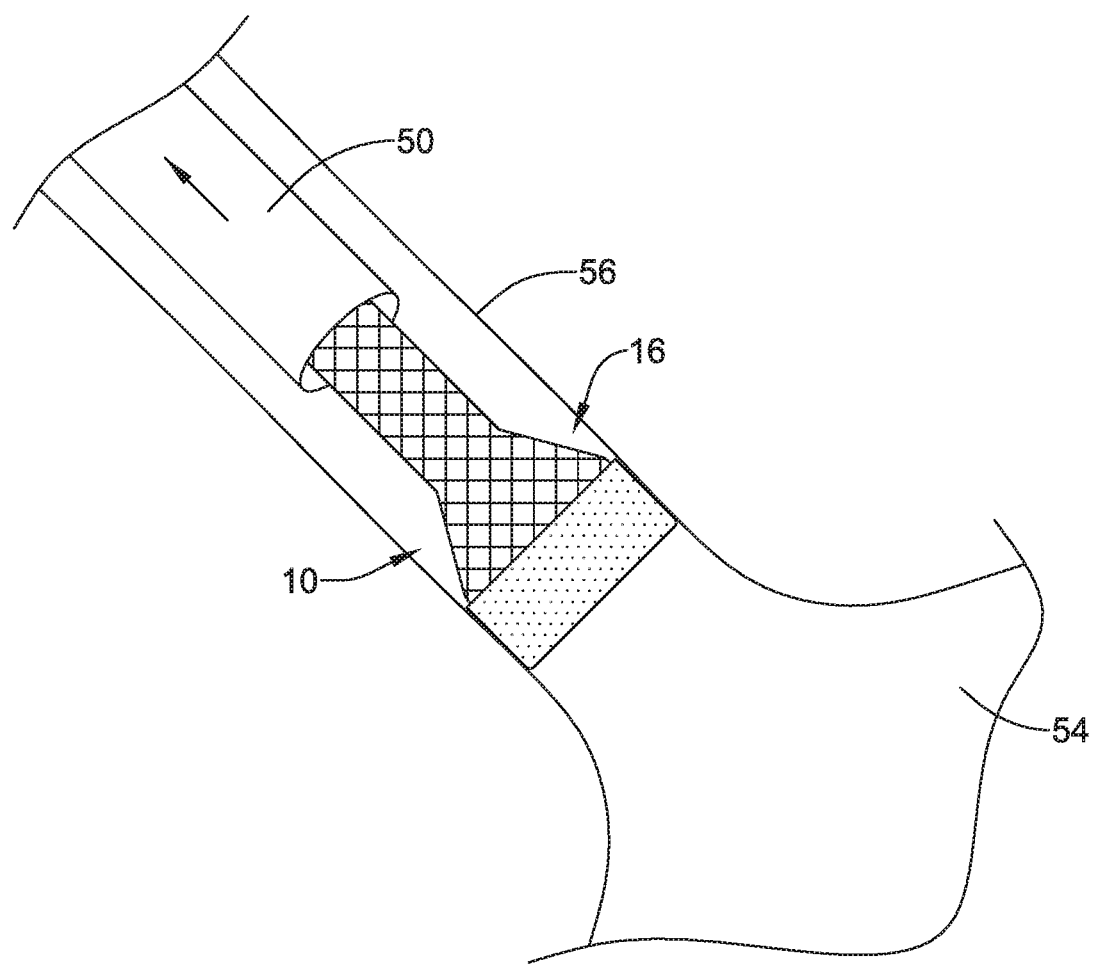

FIG. 21 illustrates and example third step in deploying stent 10 into the esophagus 56. Specifically, FIG. 21 illustrates that a clinician may retract both stent 10 and delivery device 50 proximally from the stomach into the esophagus 56 with the distal flared portion 16 deployed from delivery device 50 and radially expanded. It can be appreciated that flared portion 16 may contract from a fully expanded configuration (while in the stomach 54) to a partially contracted configuration (while in the esophagus 56) as flared portion 16 of stent 10 is retracted from the stomach 54 into the esophagus 56. The step of initially deploying flared portion 16 of stent 10 in the stomach 54 may provide an advantage of having flared portion 16 to exert a maximum force radially outward against the wall of the esophagus 56 when retracted therein.

Figure 22:
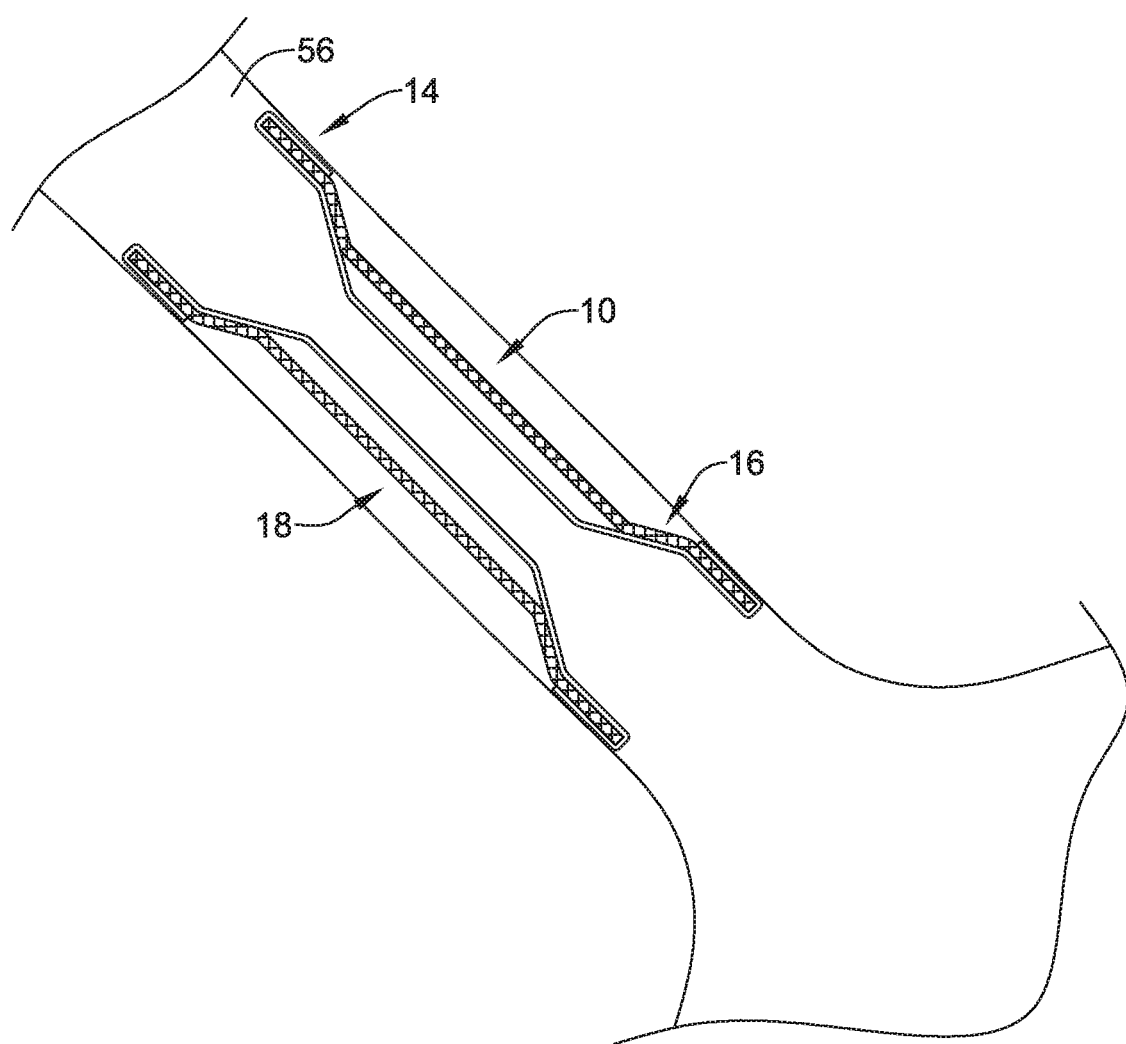

FIG. 22 illustrates an example fourth step in deploying stent 10 into the esophagus 56. Specifically, FIG. 22 illustrates that delivery device 50 (not shown in FIG. 22) has been fully retracted, thereby deploying both medial portion 18 and first flared portion 14 of stent 10 in the esophagus 56. As described above, both first flared portion 14 and second flared portion 16 may be deployed such as they create a seal along the inner surface of esophagus 56. In some instances, medial portion 18 of stent 10 may be spaced away from the inner surface of esophagus 56, however, in other instances medal portion 18 may contact inner surface of esophagus 56. After deployment of stent 10, a hyperplastic response may occur as described with respect to FIGS. 16-18 above, whereby tissue may grow into and/or through the tubular scaffold along uncovered medial portion 18 of stent 10.

The materials that can be used for the various components of stent 10 (and/or other stents disclosed herein) and the various medical devices disclosed herein may include those commonly associated with medical devices. For simplicity purposes, the following discussion makes reference to stent 10 and other components of stent 10. However, this is not intended to limit the devices and methods described herein, as the discussion may be applied to other similar medical devices disclosed herein.

Stent 10 and other components of stent 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10 and other components of stent 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into stent 10. For example, stent 10 and other components of stent 10, or portions thereof, may be made of a material that does not substantially distort the image and create substantial artifacts (e.g., gaps in the image). Stent 10 and other components of stent 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An expandable medical device, comprising:
   a tubular scaffold, the tubular scaffold including an inner surface, an outer surface, a first end region, a second end region, a medial region positioned between the first end region and the second end region, and a lumen extending from the first end region to the second end region; and
   a liner disposed within the lumen of the tubular scaffold;
   wherein the liner is secured to both the first end region and the second end region of the tubular scaffold but is radially spaced from the medial region of the tubular scaffold to define a tissue ingrowth region along the medial region between the inner surface of the tubular scaffold and an outwardly-facing surface of the liner;
   wherein a portion of the liner extending along the tissue ingrowth region is configured to limit the amount of tissue ingrowth along the medial region of the scaffold.

2. The medical device of claim 1, wherein the liner is configured to limit the amount of tissue ingrowth into the medial region of the tubular scaffold due to a hyperplastic response.

3. The medical device of claim 1, wherein the portion of the liner extending along the tissue ingrowth region is configured to deflect radially inward from the inner surface of the tubular scaffold.

4. The medical device of claim 3, wherein the medial region of the tubular scaffold includes a first inner diameter, and wherein the diameter of the liner along the tissue ingrowth region includes a second inner diameter, and wherein the second inner diameter is greater than 25% of the first inner diameter.

5. The medical device of claim 1, wherein the liner is designed to maintain a passageway therethrough.

6. The medical device of claim 1, wherein the liner is fixedly attached to at least a portion of the inner surface of the tubular scaffold along the first end region of the tubular scaffold and the liner is fixedly attached to at least a portion of the inner surface of the tubular scaffold along the second end region of the tubular scaffold.

7. The medical device of claim 1, wherein the tissue ingrowth region extends circumferentially around the inner surface of the tubular scaffold.

8. The medical device of claim 1, wherein a first portion of the liner forms an outer layer disposed along a portion of the outer surface of the tubular scaffold along the first end region, and a second portion of the liner forms an outer layer disposed along a portion of the outer surface of the tubular scaffold along the second end region.

9. The medical device of claim 1, wherein the liner is circumferentially attached to the first end region of the tubular scaffold at a first location and the liner is circumferentially attached to the second end region of the tubular scaffold at a second location, and wherein the tissue ingrowth region is defined between the first location and the second location.

10. The medical device of claim 1, wherein the tubular scaffold includes interstices extending from the outer surface of the tubular scaffold to the inner surface of the tubular scaffold, wherein the medial region is devoid of any outer covering such that tissue is permitted to grow through the interstices of the tubular scaffold along the medial region.

11. An esophageal stent, comprising:
    an expandable tubular scaffold, the tubular scaffold including an inner surface, an outer surface and a lumen extending therein; and
    a liner disposed within the lumen of the tubular scaffold;
    wherein the liner extends continuously within the lumen of the tubular scaffold;
    wherein the liner is radially spaced from a medial region of the tubular scaffold to define a tissue ingrowth region along the medial region between the inner surface of the tubular scaffold and an outwardly-facing surface of the liner;
    wherein the liner is configured to maintain a passageway through the liner for material to flow therethrough.

12. The esophageal stent of claim 11, wherein the liner is configured to limit the amount of tissue ingrowth into the medial region of the tubular scaffold due to a hyperplastic response.

13. The esophageal stent of claim 11, wherein a portion of the liner extending along the tissue ingrowth region is configured to deflect radially inward from the inner surface of the tubular scaffold.

14. The esophageal stent of claim 13, wherein the medial region of the tubular scaffold includes a first inner diameter, and wherein the diameter of the liner along the tissue ingrowth region includes a second inner diameter, and wherein the second inner diameter is greater than 25% of the first inner diameter.

15. The esophageal stent of claim 11, wherein a portion of the liner extends around at least one end of the tubular scaffold to form an outer layer disposed along a portion of the outer surface of the tubular scaffold.

16. The esophageal stent of claim 11, wherein the tubular scaffold includes interstices extending from the outer surface of the tubular scaffold to the inner surface of the tubular scaffold, wherein the esophageal stent is devoid of any outer covering radially outward of the medial region of the tubular scaffold such that tissue is permitted to grow through the interstices of the tubular scaffold along the medial region.

17. The esophageal stent of claim 11, wherein the liner is circumferentially affixed to a first end region of the tubular scaffold at a first location and the liner is circumferentially affixed to a second end region of the tubular scaffold at a second location, and wherein the tissue ingrowth region is defined between the first location and the second location.

18. An esophageal stent, comprising:
an expandable tubular scaffold having a lumen extending therein, the tubular scaffold including a first end region, a second end region and a medial region positioned between the first and the second end regions; and
a liner extending continuously within the lumen of the tubular scaffold;
wherein the liner is circumferentially attached along the first end region and the second end region, and wherein a tissue ingrowth region is defined along the medial region of the tubular scaffold;
wherein the liner is radially spaced from the medial region of the tubular scaffold to define the tissue ingrowth region along the medial region between an inner surface of the tubular scaffold and an outwardly-facing surface of the liner;
wherein the liner is configured to maintain a passageway through the liner for material to flow therethrough;
wherein the tubular scaffold is configured such that when the stent is implanted, interstices of the tubular scaffold along the medial region remain unobstructed to tissue ingrowth, thereby allowing tissue ingrowth into the tissue ingrowth region along the medial region.

19. The esophageal stent of claim 18, wherein a portion of the liner extending along the tissue ingrowth region is configured to deflect radially inward from the inner surface of the tubular scaffold.

* * * * *